(12) United States Patent
Mossalayi et al.

(10) Patent No.: US 8,071,552 B2
(45) Date of Patent: Dec. 6, 2011

(54) PEPTIDES AND PEPTIDOMIMETICS BINDING TO CD23

(75) Inventors: Mohammad Djavad Mossalayi, Bordeaux (FR); Daniel Moynet, Talence (FR); Philippe Vincendeau, Pessac (FR); Jerome Rambert, Bordeaux (FR); Christopher R. Self, Piscataway, NJ (US)

(73) Assignee: Universite Bordeaux 2, Brodeaux Cedex (FR)

( * ) Notice: Subject to any disclaimer, the term of this patent is extended or adjusted under 35 U.S.C. 154(b) by 0 days.

(21) Appl. No.: 10/594,674

(22) PCT Filed: Apr. 5, 2005

(86) PCT No.: PCT/IB2005/001133
§ 371 (c)(1),
(2), (4) Date: Feb. 13, 2007

(87) PCT Pub. No.: WO2005/098435
PCT Pub. Date: Oct. 20, 2005

(65) Prior Publication Data
US 2008/0039402 A1 Feb. 14, 2008

(30) Foreign Application Priority Data
Apr. 5, 2004 (EP) .................................... 04290899

(51) Int. Cl.
| A61K 38/08 | (2006.01) |
| A61K 38/06 | (2006.01) |
| A61K 38/07 | (2006.01) |
| A61K 38/05 | (2006.01) |
| A61K 38/12 | (2006.01) |
| A61K 39/385 | (2006.01) |

(52) U.S. Cl. .................. 514/21.1; 514/21.7; 514/21.8; 514/21.9; 514/21.91; 530/328; 530/329; 530/330; 530/331; 424/185.1; 424/193.1

(58) Field of Classification Search .................. None
See application file for complete search history.

(56) References Cited

U.S. PATENT DOCUMENTS
5,028,592 A * 7/1991 Lipton ............................. 514/18
2006/0233805 A1* 10/2006 Figdor et al. ................ 424/146.1

FOREIGN PATENT DOCUMENTS
| DE | 197 49 277 A1 | 5/1999 |
| JP | 2002 187899 A | 7/2002 |
| WO | WO 96/12741 A | 5/1996 |
| WO | WO 98/37099 A | 8/1998 |
| WO | WO 03/064457 A | 8/2003 |
| WO | WO 2004/026326 A | 4/2004 |
| WO | WO 2005/019258 A | 3/2005 |

OTHER PUBLICATIONS

Stryer et al, in Biochemistry, Third edition, W H Freeman Company, New York, pp. 31-33, 1998.*
Ngo et al, The Protein Folding Problem and Tertiary Structure Prediction, pp. 491-495, 1994.*
Van Noort et al, International Review of Cytology 178: 127-205, 1998.*
Heck et al, Proc Natl Acad Scie 93:4036-4039, Apr. 1996.*
Harlow et al, in Antibodies a Laboratory Manual, 1988, Cold Spring harbor laboratory publication, Cold Spring Harbor, NY, p. 321-323.*
Jouault, T., et al; "Peptides That Mimic Candida Albicans-Derived Beta-1,2-Linked Mannosides"; *Glycobiology, IRL Press, GB*; vol. 11, No. 8, pp. 693-701; Aug. 2001; XP009026488.
Santamaria, H., et al; "Identification of peptide sequences specific for serum antibodies from human papillomavirusinfected patients using phage display libraries"; *Clinical Immunology (Orlando)*; vol. 101, No. 3, pp. 296-302; Dec. 2001; XP009045311.
Anni, H., et al; "Selection of phage-display library peptides recognizing ethanol targets on proteins"; *Alcohol* (Fayetteville, NY); vol. 25, No. 3; pp. 201-209; Nov. 2001; SP009045307.
Miura, Y., et al; "Peptides binding to a Gb3 mimic selected from a phage library"; *BBA—General subjects, Elsevier Science Publishers, NL*; vol. 1673, No. 3; pp. 131-138; Aug. 4, 2004; XP004523265.
Gloeckner, et al; Database EMBL (Online); Oct. 1, 2003; Database Accession No. Q7USF5; XP002321307.
Galagan, et al; Database EMBL (Online); Mar. 1, 2004; Database Accession No. Q7RYN4; XP002321308.
Chaudhary, et al; Database EPO Proteins (Online); Jun. 14, 2002; Database Accession No. AX411500; XP002321309.
Chaconas, et al; Database GENESEQ (Online); Feb. 12, 2004; Database Accession No. ADF72653; XP002321310.
Beasley, et al; Database EPO Proteins (Online); Oct. 26, 2001; Database Accession No. AX256979; XP002321311.

* cited by examiner

*Primary Examiner* — Phuong Huynh
(74) *Attorney, Agent, or Firm* — Nixon & Vanderhye

(57) ABSTRACT

The present invention describes compounds comprising new and useful peptides and peptidomimetics that can bind to CD23. They are capable of reducing inflammatory responses associated with auto-immune diseases, chronic inflammatory diseases, allergies and other inflammatory conditions such as those mediated by the mammalian immune system. Compounds of the present invention relate to a CD23-binding peptide wherein said peptide comprises an amino-acid sequence of $X_1$—$X_2$—$X_3$—$X_4$—$X_5$—$X_6$—$X_7$—$X_8$, wherein: $X_1$ is Phe, or is absent; $X_2$ is His or Ala; $X_3$ is Glu, Ser, Ala, Asn, Lys, or Cys; $X_4$ is Asn, Phe, Gln, Pro, Ser, or Ala; $X_5$ is Trp; $X_6$ is Pro, Arg, Glu, Gly, Cys, or Lys; $X_7$ is Ser, Pro, Leu, Thr Ala, Gly, Asn, or absent; and $X_8$ is Phe, Gly, or is absent.

5 Claims, 4 Drawing Sheets a = before treatment
b = after treatment

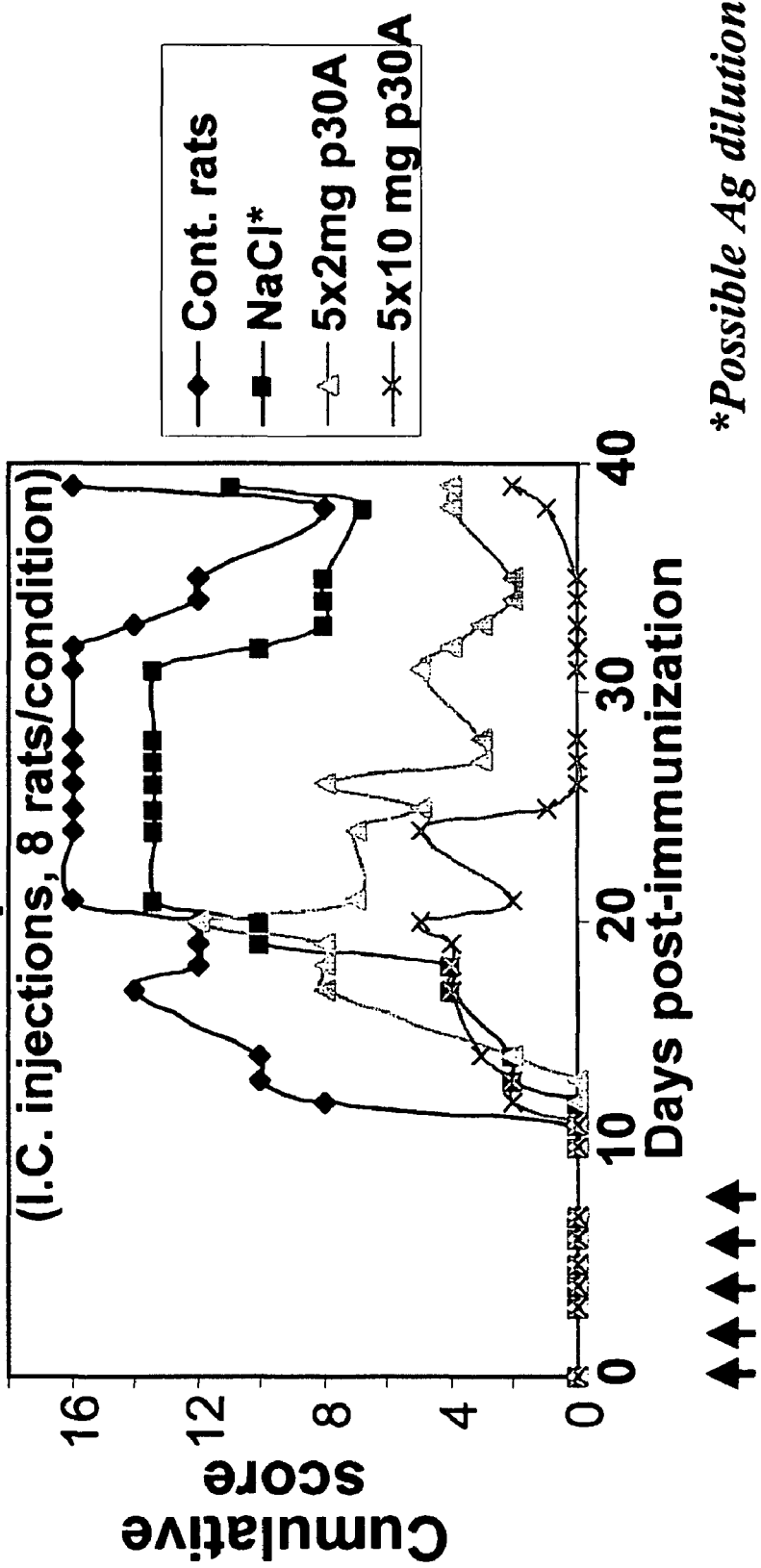

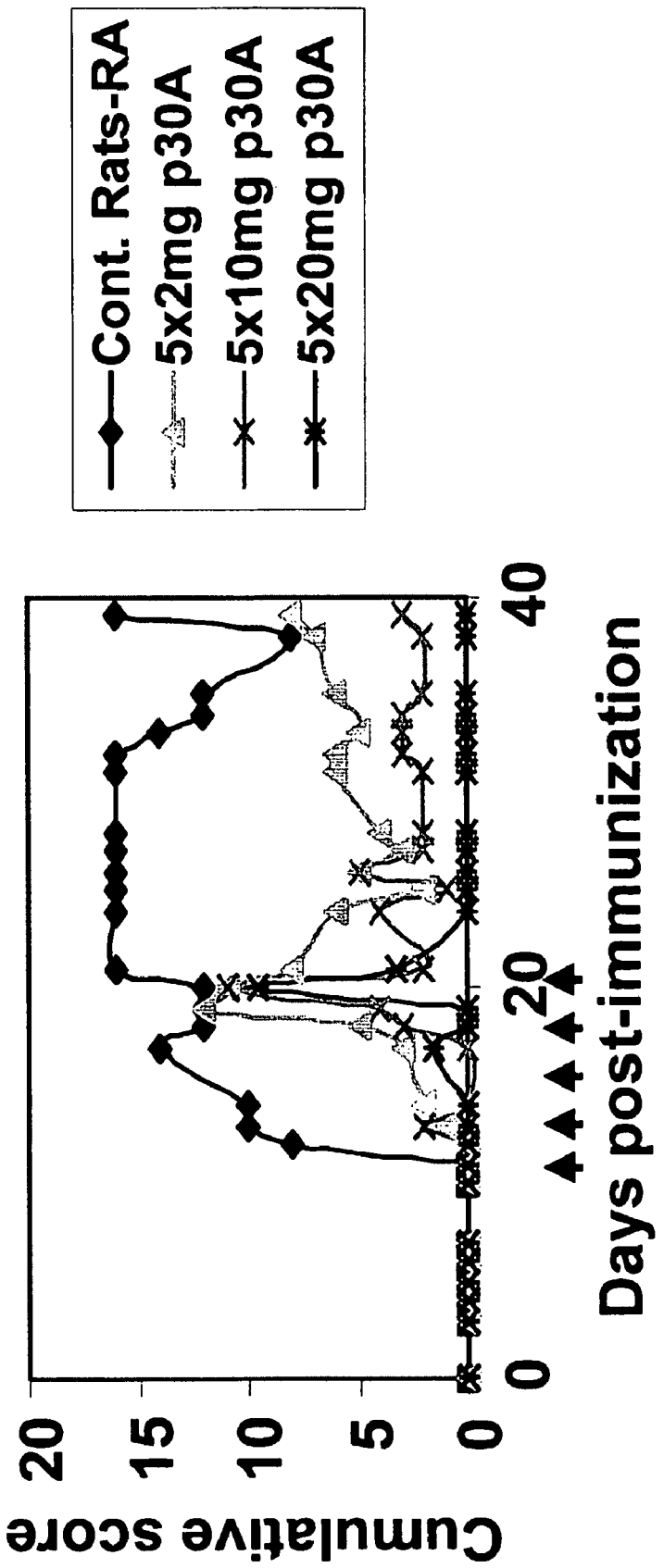

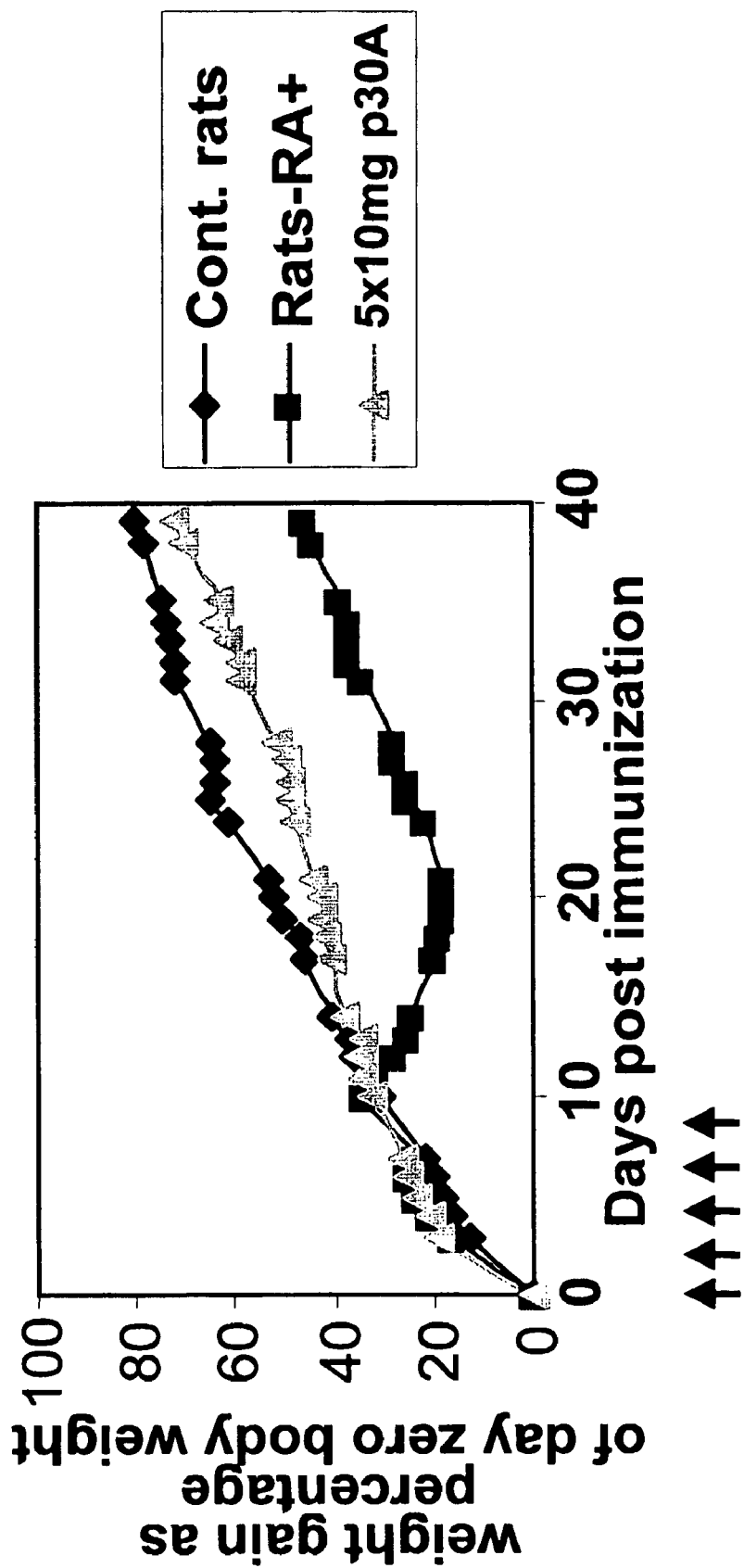
Fig. 4 Weight increase in rats following I.C. treatment with p30A (5x10 mg)

PEPTIDES AND PEPTIDOMIMETICS BINDING TO CD23

This application is the U.S. National Phase of International Application PCT/IB2005/001133, filed 5 Apr. 2005, which designated the U.S. PCT/IB2005/001133 claims priority to European Application No. 04290899.6 filed 5 Apr. 2004. The entire content of these applications are incorporated herein by reference.

FIELD OF THE INVENTION

The present invention relates to new peptides and peptidomimetics which bind to the CD23 (FCεRII) molecule, pharmaceutical compositions which contain such peptides and peptidomimetics, and their use in therapy.

Reported Developments

CD23, initially described as the low affinity receptor for IgE (FCεRII) on B lymphocytes, has been subsequently found on subsets of monocytes/macrophages, eosinophils, platelets, T cells, as well as epithelial cells, upon their in vitro or in vivo activation. CD23 is a type II molecule of the C-type lectin family. Soluble CD23 (sCD23) molecules are formed by proteolytic cleavage of transmembrane receptors. CD23 has pleiotropic activities including mediation of cell adhesion, regulation of IgE and histamine release, rescue of B-cells from apoptosis and regulation of myeloid and lymphoid cell growth. These functional activities are mediated through the binding to specific ligands of cell-associated CD23 or sCD23, the latter acting in a cytokine-like manner. In addition to IgE, CD23 has the ability to bind various biologic ligands such as CD21, CD11b/c, integrins, CD47/vitronectin and glycoproteins that trigger its lectin domain. CD23 is encoded by a single gene located on human chromosome 19. This gene has about 13 kb and consists of 11 exons. Two isoforms, which differ by six amino acids, CD23a and CD23b, are encoded by the human CD23 gene. CD23a is expressed by B-cell lineage, whereas CD23b is found on B and other human cells.

The majority of human inflammatory diseases imply the activation of macrophages, directly or indirectly through their ability to produce various mediators. Most anti-inflammatory therapies were established to inhibit the function of these cells or to inhibit one of their products. Several factors activate macrophages, including infectious agents, tumour cells, cytokines, cell lysates. Macrophages may also be activated by other cells or extracellular molecules following the ligation of surface receptors, such as CD23. CD23 is expressed by nearly all macrophages, including various organ specific macrophagic cells (e.g., Kupffer cells, Microglia, Langerhans cells). High surface density of CD23 on activated macrophages, eosinophils and human epithelial cells allows various physiologic ligands to crosslink these molecules and to activate inflammatory functions of target cells. This phenomenon has been shown to mediate the elimination of intracellular and extracellular parasites by human macrophages. CD23 stimulation also promotes the generation of TNF-α, IL-1, IL-6, leukotriens, oxygen-derived species and nitric oxide (NO) by human macrophages, eosinophils, epithelial cells and rat macrophages. Following proteolysis, soluble CD23 is released in vivo and is detected in normal human sera. This form of CD23 is also shown to induce various immune responses, including the activation of macrophages and B-cells, following the ligation of its counter-structures on these cells. Both surface and soluble CD23 have a critical role during inflammation. High expression of CD23 or its soluble form is a common marker of various allergic, auto-immune, infectious and other inflammatory diseases (Aubry J.-P. et al, Nature, 358, 505-507 (1992); Bonnefoy J.-Y. et al, Int. Rev. Immunol. 16, 113-128 (1997); Hermann P. et al J. Cell. Biol. 144, 767-775 (1999); Mossalayi et al, Int. Rev. Immunol. 16, 129-146 (1997)).

CD23 plays a critical role in rheumatoid arthritis (Plater-Zyberk and Bonnefoy, Nature Medicine, vol. 1, 8, 781-785 (1995), allergic responses (Kleinau S. et al, Journal of Immunology, 162, 4266-4270 (1999)), and the regulation of IgE synthesis (L. Flores-Romo et al., Science, 261, 1038-1041 (1993); Aubry J.-P. et al, Nature, 358, 505-507 (1992)). A cytokine/CD23-dependant activation pathway affects the induction of nitric oxide synthase and expression of pro-inflammatory mediators in glial cells. CD23 expression is also required for B-chronic lymphocytic leukaemia (B-CLL) cell survival (Mavromatis and Cheson, Journal of Clinical Oncology. 21:1874-1881, (2003)) and plays a role in Parkinson's disease, (Hunot S. et al, The Journal of Neuroscience, 19(9), 3440-3447 (1999)

SUMMARY OF THE INVENTION

The present invention relates to a compound comprising a CD23-binding peptide wherein said peptide comprises an amino-acid sequence of $X_1$—$X_2$—$X_3$—$X_4$—$X_5$—$X_6$—$X_7$—$X_8$, wherein:

$X_1$ is Phe, or is absent;
$X_2$ is His or Ala;
$X_3$ is Glu, Ser, Ala, Asn, Lys, or Cys;
$X_4$ is Asn, Phe, Gln, Pro, Ser, or Ala;
$X_5$ is Trp;
$X_6$ is Pro, Arg, Glu, Gly, Cys, or Lys;
$X_7$ is Ser, Pro, Leu, Thr, Ala, Gly, Asn, or absent; and
$X_8$ is Phe, Gly, or is absent.

The present invention also relates to chemically modified peptides and peptidomimetics of the CD23-binding peptide described above.

BRIEF DESCRIPTION OF THE DRAWING

FIG. 2. Preventive effect of treatment of rats with p30A.

FIG. 3. Therapeutic effect of treatment of rats with p30A.

FIG. 4. Weight gain of control rats, rats with rheumatoid arthritis (RA) treated with p30A, and rats with RA left untreated.

DETAILED DESCRIPTION OF THE INVENTION

Figure 1:
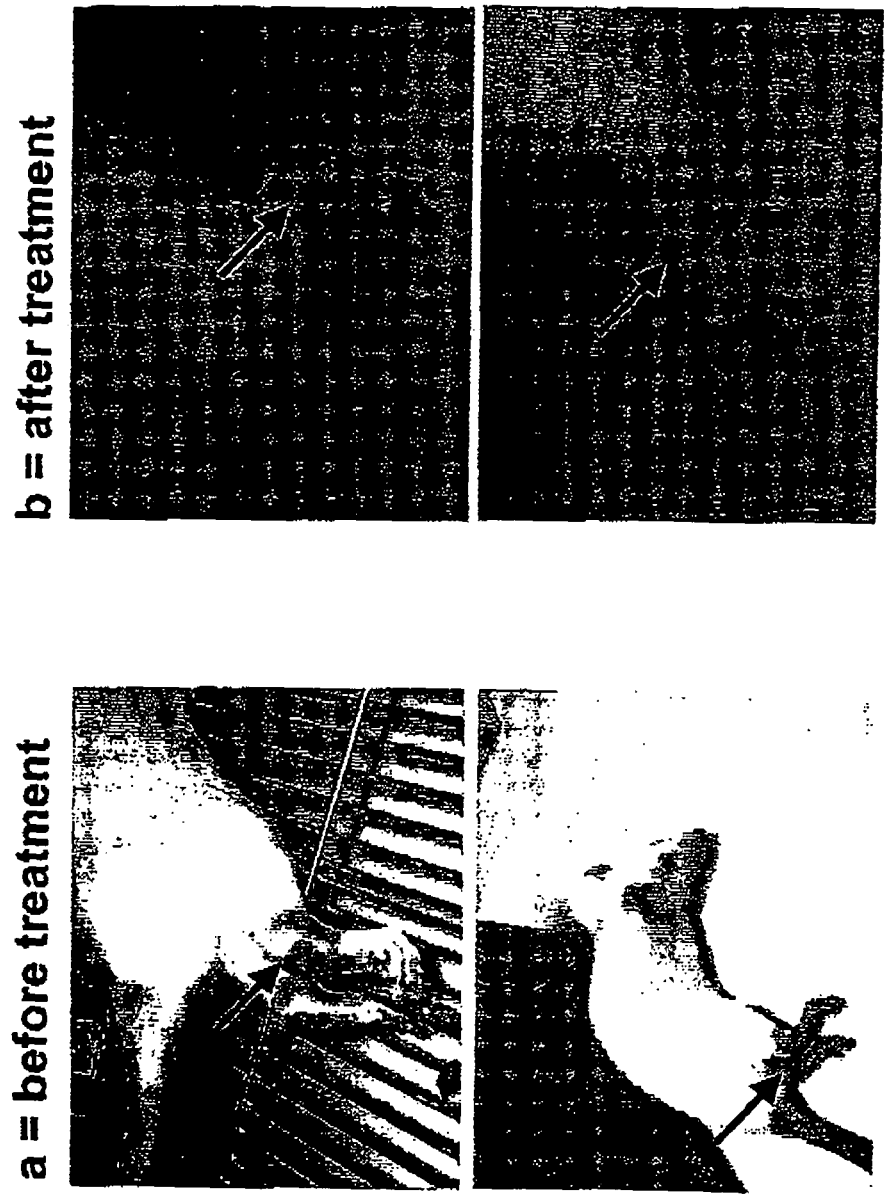
FIG. 1. (a) Following immunization with heat-inactivated *Mycobacterium butyricum*, rats show arthritis signs by day 15-21. (b) Subcutaneous injection of 5 mg of FHENWPS peptide (SEQ ID NO: 1; p30A) results in remission.

The present invention provides compounds which are selectively directed to the prophylaxis and treatment of auto-immune diseases, acute and chronic inflammatory diseases, allergies and B-CLL. The invention is based in part on the discovery of compounds which bind to CD23 and inhibit CD23's binding to its natural ligands. As CD23 is expressed on activated macrophages or epithelial cells, and as soluble CD23 is involved in auto-immune diseases, inflammatory chronic diseases and allergies, it is believed that such compounds can be used for treatment and prophylaxis of these diseases. However, the blockage of CD23 does not prevent the activation of macrophages through their other receptors. This strategy therefore does not result in a general inhibition of immune response in contrast to present commercial anti-inflammmatory treatments. The compounds which are the object of the present invention have also been designed to bind to soluble CD23, so that the activation of macrophages by sCD23 is also inhibited.

Antibodies to CD23, fragments and derivatives thereof and their use in the treatment of inflammatory, autoimmune or allergic diseases have been described in PCT Applications WO96/12741 and WO99/58679. However, there remains a need for compounds that are easy to prepare and that can be produced by using a chemical route, thus avoiding the presence of bio-contaminants. Antibodies block the immune system and are mostly immunogenic with the side effects associated with such a mechanism. Accordingly a need remains for compounds capable of modulating the immune response.

Compounds which include amino acid derivatives and peptide derivatives comprising at most two amino acids, and their use as inhibitors of the release of human soluble CD23 are described in PCT Application WO96/02240. Such compounds are useful in the treatment and prophylaxis of conditions in which an excess of CD23 is implicated such as allergy and auto-immune diseases. PCT Applications WO97/43249, WO01/49657, WO01/62715, WO01/85721, WO01/90100 also disclose inhibitors of the formation of soluble CD23 and their use in the treatment of conditions associated with the production of soluble CD23 such as auto-immune diseases, inflammation and allergy. However the target of these molecules is different from the target of the compounds according to the present invention and they differ in their structure from the compounds according to the present invention.

Anti-inflammatory peptides have been described in the past. Peptides have been described that mimic immunoglobulin fragments and can block the binding of the related immunoglobulin to Fc receptors: Ratcliffe and Stanworth, (Immunol. Lett., 4, 215 (1982) have demonstrated that a peptide identical to IgG aa 215-301 (Gln-Tyr-Asp-Ser-Thr-Tyr-Arg) could slightly block IgG binding to human monocyte IgG Fc receptors. Hamburger (Science, 189, 389 (1975); U.S. Pat. No. 4,171,299; U.S. Pat. No. 4,161,522) has reported that a pentapeptide with sequence derived from human IgE Cε3 at aa 320-324 (Asp-Ser-Asp-Pro-Arg) could inhibit a local cutaneous allergic reaction by approximately 90%. This peptide has subsequently been shown to inhibit systemic allergic diseases in humans. It has also been demonstrated that this peptide has significant affinity for the IgE Fc receptors (Plummer et al, Fed. Proc., 42, 713 (1983); Hamburger, Adv. Allergology Immunol., Pergamon Press, New York, 591-593 (1980)). A hexapeptide derived from IgE CE4 at aa 476-481 has been reported to block IgE binding to IgE Fc receptors (Hamburger, Immunology, 38, 781 (1979); U.S. Pat. No. 4,161,522). Peptides that can block the binding of IgG and IgE immune complexes to IgG Fc and IgE Fc receptors are described in U.S. Pat. No. 4,579,840. Peptides bearing a structural similarity to the Cε3 aa 320-324 portion of human IgE have been demonstrated to interact directly in the arachidonic acid-mediated inflammatory pathway and reduce such inflammation (U.S. Pat. No. 4,816,449).

However, these peptides are structurally different from those according to the present invention and none of these peptides has been described as having an affinity with CD23.

The present invention describes sequences of new and useful peptides that can bind to CD23. They are capable of reducing inflammatory responses associated with auto-immune diseases, chronic inflammatory diseases, allergies and other inflammatory conditions such as those mediated by the mammalian immune system. Peptides according to the present invention are able to modulate the immune response of cells. They are less immunogenic than antibodies, they are available as a synthetic product, therefore free of bio contaminants.

Amino acids which may be incorporated into the peptides include all of the commonly occurring amino acids. Two designations for amino acids are used interchangeably throughout this application, as is common practice in the art: Alanine=Ala (A); Arginine=Arg (R); Aspartic Acid=Asp (D); Asparagine=Asn (N); Cysteine=Cys (C); Glutamic Acid=Glu (E); Glutamine=Gln (Q); Glycine=Gly (G); Histidine=His (H); Isoleucine=Ile (I); Leucine=Leu (L); Lysine=Lys (K); Methionine=Met (M); Phenylalanine=Phe (F); Proline=Pro (P); Serine=Ser (S); Threonine=Thr (T); Tryptophan=Trp (W); Tyrosine=Tyr (Y); Valine=Val (V).

Any of the so-called rare or modified amino acids may also be incorporated into a peptide of the invention, including but not limited to the following: 2-Aminoadipic acid, 3-Aminoadipic acid, beta-Alanine (beta-Aminopropionic acid), 2-Aminobutyric acid, 4-Aminobutyric acid (piperidinic acid), 6-Aminocaproic acid, 2-Aminoheptanoic acid, 2-Aminoisobutyric acid, 3-Aminoisobutyric acid, 2-Aminopimelic acid, 2,4-Diaminobutyric acid, Desmosine, 2,2'-Diaminopimelic acid, 2,3-Diaminopropionic acid, N-Ethylglycine, N-Ethylasparagine, Hydroxylysine, allo-Hydroxylysine, 3-Hydroxyproline, 4-Hydroxyproline, Isodesmosine, allo-Isoleucine, N-Methylglycine (sarcosine), N-Methylisoleucine, N-Methylvaline, Norvaline, Norleucine, Omithine, 2-Napthylalanine, Threoninol, Tetrahydroisoquinoline 3-carboxlic acid, 4-Indoyl alanine, beta-Tryptophan, cyclo-Leucine.

The compositions of the invention may include a peptide modified to render it biologically protected. Biologically protected peptides have certain advantages over unprotected peptides when administered to human subjects and, as disclosed in U.S. Pat. No. 5,028,592 (incorporated herein by reference), protected peptides often exhibit increased pharmacological activity, as was found to be true in the present case.

The present invention therefore also encompasses compositions comprising an acylated peptide or peptides, and preferably, a peptide acylated at the N-terminus. Virtually any acyl group may be employed in this context but the addition of an acetyl group (Ac) to the N-terminus of a given peptide is preferred. The inhibitory peptide compositions may also include a peptide(s) which is amidated at the C-terminus, i.e., to which an $NH_2$ group has been added. In particularly preferred embodiments, peptides which have both an acylated N-terminal and an amidated C-terminal residue are preferred. Suitable chemical derivatives of the peptides according to the invention include des-alpha amino peptides, N-alpha acyl substituent of the form RCO—, where R is an alkyl, alkenyl, alkynyl, aryl or aralkyl group, linear, branched, or cyclic comprising 1 to 50, preferentially 1 to 8 carbon atoms. R can also be a residue of a polyose or a protein. Preferred N-alpha acyl substituent is the acetyl group. Such amino-terminal substituents may increase peptide activity by preventing or slowing the course of enzymatic degradation of the peptides in the in vivo environment.

Other chemical derivatives of the peptides of the present invention include C-terminal alkyloxy, alkylthio, or alkylamino substituents in which the carboxyl group is replaced by —COOR, —COSR, —$CONH_2$—CONHR, where R is a group chosen to facilitate the in vivo penetration of the peptide and its reaching its target. For example, R can be a long chain alkyl, alkenyl, alkynyl, aryl or aralkyl group, linear, branched, or cyclic comprising 1 to 50, preferably 8 to 50 carbon atoms, R can also be a residue of a polyose or a protein.

Further chemical derivatives of the peptides of the present invention include those bearing a substituent which allows the detection of the peptide, notably a fluorescent group such as green fluorescent protein (GFP) (Daly and McGrath, Pharmacology and therapeutics, 100:101-118, (2003)).

Preferentially, according to the invention, the amino-acid from which the peptides are made are L-enantiomers. However, one or more of the amino-acids of the sequence can be replaced by their D-enantiomers without activity modulation. This will also will prevent or reduce enzymatic degradation.

The present invention relates to a compound comprising a CD23-binding peptide wherein said peptide comprises an amino-acid sequence of $X_1-X_2-X_3-X_4-X_5-X_6-X_7-X_8$, wherein:

$X_1$ is Phe, or is absent;
$X_2$ is His or Ala;
$X_3$ is Glu, Ser, Ala, Asn, Lys, or Cys;
$X_4$ is Asn, Phe, Gln, Pro, Ser, or Ala;
$X_5$ is Trp;
$X_6$ is Pro, Arg, Glu, Gly, Cys, or Lys;
$X_7$ is Ser, Pro, Leu, Thr, Ala, Gly, Asn, or absent; and
$X_8$ is Phe, Gly, or is absent.

In a preferred embodiment the CD23-binding peptide is selected from the group consisting of SEQ ID NO: 1-10.

As used herein, the term amino acid is used in its broadest sense to mean the naturally occurring as well as the non-naturally occurring amino acids, including amino acid analogues. Thus, reference to amino acids includes (L)-amino acids as well as (D)-amino acids, chemically modified amino acids, naturally occurring, non proteogenic amino acids such as norleucine, homoarginine, ornithine, 2' napthyl alanine, tetrahydrolsoquinoline-3-carboxylic acid, 4' indolyl alanine, threoninol, (S) 3-amino 4-(3-indoyl)butyric acid, 1-amino cyclopentane-1-carboxylic acid, beta alanine, homo proline, tetrahydronorharman-3-carboxylic acid, citruline, 2,3-diaminoproprionic acid, 4' thiazoyl alanine, 3-(imadazol-4-yl) proprionic acid, 1-N-methyl histidine, N-methyl glycine, 1-(amino methyl) cyclopentane-1-carboxylic acid and chemically synthesised compounds having properties known in the art to be characteristic of an amino acid. As used herein, the term proteogenic indicates that the amino acid can be incorporated into a protein in a cell through a metabolic pathway. Among chemically modified amino acids that can be used according to the present invention are included for example amino acids bearing a fluorescent group (e.g., GFP) that will allow the detection of the peptide or amino acids and amino acids in which the central C is replaced by a Si atom or a Sn atom.

The present invention also relates to peptides comprising the above amino acid sequence(s) except that they contain one or more conservative amino acid substitutions. A "conservative amino acid substitution" is one in which the amino acid is replaced with an amino acid residue having a similar side chain. Families of amino acids having similar side chains have been defined in the art. These families include amino acids with basic side chains (e.g., lysine, arginine, histidine), acidic side chains (e.g., aspartic acid, glutarnic acid), uncharged polar side chains (e.g., glycine, asparagine, glutamine, serine, threonine, tyrosine, cysteine), non-polar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a polypeptide comprising an amino acid sequence at least about 83% identical (i.e., 5 out of 6 amino acids are identical) to an amino acid sequence of SEQ ID NO: 1-10 is within the scope of the present invention.

The present invention also relates to peptidomimetics of the above peptides. A "peptidomimetic" is a compound that mimics the biological activity of a peptide but is no longer peptidic in chemical nature. A peptidomimetic is a compound that may no longer contain any peptide bonds (that is, amide bonds between amino acids). The term peptidomimetic as used herein includes within its meaning compounds that are no longer completely peptidic in nature, such as pseudo-peptides, semi-peptides and peptoids. Whether completely or partially non-peptide, peptidomimetics according to this invention provide a spatial arrangement of reactive chemical moieties that closely resembles the three-dimensional arrangement of active groups in the peptide on which the peptidomimetic is based. As a result of this similar active-site geometry, the peptidomimetic has effects on biological systems which are similar to the biological activity of the peptide.

The present invention encompasses peptidomimetic compositions which are analogs that mimic the activity of biologically active peptides according to the invention, i.e., the peptidomimetics are capable of binding to CD23. The peptidomimetics of this invention are preferably substantially similar in both three-dimensional shape and biological activity to the peptides set forth above. Substantial similarity means that the geometric relationship of groups in the peptide that interact with CD23 is preserved and at the same time, that the peptidomimetic will interfere with the binding of other molecules to the CD23 molecule.

There are advantages for using a peptidomimetic rather than the peptide itself, because some peptides exhibit two undesirable properties: (1) poor bioavailability; and (2) short duration of action. Peptidomimetics offer a means to overcome these two major obstacles, since the compounds concerned are small enough to be both orally active and have a long duration of action. There are also considerable cost savings and improved patient compliance associated with peptidomimetics, since they can be administered orally compared with parenteral administration for peptides. Furthermore, peptidomimetics are much cheaper to produce than peptides. Finally, there are problems associated with stability, storage and immunoreactivity for peptides that are not experienced with peptide mimetics.

Thus the peptides described above have utility in the development of such small chemical compounds with similar biological activities and therefore with similar therapeutic utilities. The techniques of developing peptidomimetics are conventional. Thus, peptide bonds can be replaced by non-peptide bonds that allow the peptidomimetic to adopt a similar structure, and therefore biological activity, to the original peptide. Further modifications can also be made by replacing chemical groups of the amino acids with other chemical groups of similar structure. The development of peptidomimetics can be aided by determining the tertiary structure of the original peptide, either free or bound to CD23, by NMR spectroscopy, crystallography and/or computer-aided molecular modelling. These techniques aid in the development of novel compositions of higher potency and/or greater bioavailability and/or greater stability than the original peptide (Dean, BioEssays, 16: 683-687 (1994); Cohen and Shatzmiller, J. Mol. Graph., 11: 166-173 (1993); Wiley and Rich, Med. Res. Rev., 13: 327-384 (1993); Moore, Trends Pharmacol. Sci., 15: 124-129 (1994); Hruby, Biopolymers, 33: 1073-1082 (1993); Bugg et al., Sci. Am., 269: 92-98 (1993), all incorporated herein by reference). Once a potential peptidomimetic compound is identified, it may be synthesized and assayed using the methods described herein or another appropriate CD23 binding assay to assess its activity.

In peptidomimetics according to the invention, one or more amide linkages (—CO—NH—) can be replaced with another linkage which is an isostere such as: —CH$_2$NH—, CH$_2$S—, —CH$_2$CH$_2$—, —CH═CH—(cis and trans), —COCH$_2$—, —CH(OH)CH$_2$— and —CH$_2$SO—. This replacement can be made by methods known in the art (see for example, Spatola, Vega Data, Vol. 1, issue 3 (1983); Spatola, Chemistry and Biochemistry of Amino Acids Peptides and Proteins, Weinstein, ed., Marcel Dekker, New York, p. 267 (1983). Morley. J.-S., Trends Pharm. Sci., 463-468 (1980); Hudson et al, Int. J. Pept. Prot. Res. 14, 177-185 (1979); Spatola et al, Life Sci., 38, 1243-1249 (1986); Hann, J. Chem. Soc. Perkin Trans. I 307-314 (1982); Almquist et al, J. Med. Chem., 23, 1392-1398 (1980); Holladay et al, Tetrahedron Lett. 24, 4401-4404 (1983); and Hruby et al, Life Sci. 31, 189-199 (1982)).

Thus, through use of the methods described above, the present invention provides peptidomimetic compounds exhibiting enhanced therapeutic activity in comparison to the peptides on which these peptidomimetic compounds are based. The peptidomimetic compounds having the biological activity of the peptides and similar three dimensional structure, are encompassed by this invention. It will be readily apparent to one skilled in the art that a peptidomimetic can be generated from any of the modified peptides or from a peptide bearing more than one of the modifications described in the previous section. It will furthermore be apparent that the peptidomimetics of this invention can be further used for the development of even more potent non-peptidic compounds, in addition to their utility as therapeutic compounds. In a preferred embodiment the present invention provides a peptide or peptidomimetic selected from the group consisting of those peptides or peptidomimetics listed in Table 1 or Table 2. In a particularly preferred embodiment the present invention provides a peptidomimetic comprising the structure Ac-w-n-CO$_2$H.

Specific examples of peptidomimetics derived from the peptides described in the previous section are presented below in Tables 1 and 2. These examples are illustrative and not limiting in terms of the other or additional modifications.

Peptides with a Reduced Isostere Pseudopeptide Bond

Proteases act on peptide bonds. It therefore follows that substitution of peptide bonds by pseudopeptide bonds confers resistance to proteolysis. A number of pseudopeptide bonds have been described that in general do not affect peptide structure and biological activity. The reduced isostere pseudopeptide bond is a suitable pseudopeptide bond that is known to enhance stability to enzymatic cleavage with no or little loss of biological activity (Couder, et al., Int. J. Peptide Protein Res., 41:181-184 (1993), incorporated herein by reference). Thus, the amino acid sequences of these peptides may be identical to the sequences of the L-amino acid peptides described above, except that one or more of the peptide bonds are replaced by an isostere pseudopeptide bond. Preferably the most N-terminal peptide bond is substituted, since such a substitution would confer resistance to proteolysis by exopeptidases acting on the N-terminus. The synthesis of peptides with one or more reduced isostere pseudopeptide bonds is known in the art (Couder, et al., Int. J. Peptide Protein Res., 41:181-184 (1993), incorporated herein by reference).

Peptides with a Retro-Inverso Pseudopeptide Bond

The stereochemistry of polypeptides can be described in terms of the topochemical arrangement of the side chains of the amino acid residues about the polypeptide backbone which is defined by the peptide bonds between the amino acid residues and the a-carbon atoms of the bonded residues. In addition, polypeptide backbones have distinct termini and thus direction.

The majority of naturally occurring amino acids are L-amino acids. Naturally occurring polypeptides are largely comprised of L-amino acids.

D-amino acids are the enantiomers of L-amino acids and form peptides which are herein referred to as inverso peptides, that is, peptides corresponding to N-terminus to C-terminus sequence of native peptides but made up of D-amino acids rather than L-amino acids. A partial inverso peptide is one which is made up of both L- and D-amino acids.

Retro peptides, are made up of L-amino acids in which the amino acid residues are assembled in opposite direction to the native peptide sequence.

Retro-inverso modification of naturally occurring polypeptides involves the synthetic assemblage of amino acids with a-carbon stereochemistry opposite to that of the corresponding L-amino acids, i.e. D- or D-allo-amino acids, in reverse order with respect to the native peptide sequence. A retro-inverso analogue thus has reversed termini and reversed direction of peptide bonds while approximately maintaining the topology of the side chains as in the native peptide sequence.

Partial retro-inverso peptide analogues are polypeptides in which only part of the sequence is reversed and replaced with enantiomeric amino acid residues. Since the retro-inverted portion of such an analogue has reversed amino and carboxyl termini, the amino acid residues flanking the retro-inverted portion are replaced by side-chain-analogous a-substituted geminal-diaminomethanes and malonates, respectively.

Processes for synthesis of retro-inverso peptide analogues have been described (Bonelli, F., Pessi, A. & Verdini, A. S. Int. J. Peptide Protein Res., 24, 553-556 (1984); Verdini, A. S. & Viscomi, G. C. J. Chem. Soc. Perkin Trans. I, 697-701 (1985)). Processes for the solid-phase synthesis of partial retro-inverso peptide analogues are also known (Pessi, A., Pinori, M., Verdini, A. S. & Viscomi, G. C. European Patent 97994-B, Sep. 30, 1987 (8739)).

Thus, compositions for use in the present invention may comprise peptides which include all L-amino acids, all D-amino acids or a mixture thereof. The finding that peptides composed entirely of D-amino acids have potent inhibitory activity is particularly important as such peptides are known to be resistant to proteases naturally found within the human body and are less immunogenic and can therefore be expected to have longer biological half lives. According to this modification, the amino acid sequences of the peptides may be identical to the sequences of the L-amino acid peptides described above (e.g., SEQ ID NO: 1-10), except that one or more of the amino acid residues are replaced by D-enantiomer amino acids. For instance, the most N-terminus peptide bond can be inverted or retroinverted, since such an inversion or retro-inversion of this bond will increase resistance to proteolysis by exopeptidases acting on the N-terminus. Furthermore, a retro-inverted form (all D-enantiomers) of any of the disclosed all L-enantiomer peptides would have N- and C-termini reversed. For example, the retro-inverted form of the all L-enantiomer peptide NH$_2$—HENWPS—COOH would be NH$_2$-spwneh-COOH (as is common practice in the art, D-enantiomers of amino acids are designated by lower case). The synthesis of peptides with one or more reduced retro-inverso pseudopeptide bonds is known in the art (Dalpozzo, et al. Int J Pept Protein Res. 41(6):561-6 (1993)).

Peptoid Derivatives

Peptoid derivatives of peptides represent another form of modified peptides that retain the important structural determinants for biological activity, yet eliminate the peptide bonds, thereby conferring resistance to proteolysis (Simon, et al., Proc. Natl. Acad. Sci. USA, 89:9367-9371 (1992)) and incorporated herein by reference). Peptoids are oligomers of N-substituted glycines. A number of N-alkyl groups have been described, each corresponding to the side chain of a natural amino acid (Simon, et al., Proc. Nat). Acad. Sci. USA, 89:9367-9371 (1992)). Furthermore, not all of the amino acids have to be replaced. For example, the N-terminal residue may be the only one that is replaced, or a few amino acids may be replaced by the corresponding N-substituted glycines.

Longer peptides comprising a sequence according to the present invention and capable of binding to CD23 molecules are also included in the scope of the present invention. The longer peptides may comprise any amino acid sequence bound to either the N-terminal or C-terminal or both of a peptide of the present invention including SEQ ID NO: 1-10. Preferentially, they have about 100 or less amino acids, more suitably about 70 or less amino acids, preferably about 50 or less amino acids, more preferably about 30 or less amino acids, and even more preferably about 15 or less amino acids, in total. As indicated above, the minimum length is about 6.

The capacity for a peptide or a peptidomimetic compound according to the invention to bind to CD23 can be assessed by a test described in detail in Examples 4 to 7. However a peptide or a peptidomimetic compound is considered to bind to CD23 according to the present invention if it has a specific binding activity of about $K_d$=less than $10^{-6}$, preferably between $10^{-6}$ and $10^{-11}$M.

Preferred peptide compounds according to the invention are those corresponding to SEQ ID NO: 1-10:

```
Phe-His-Glu-Asn-Trp-Pro-Ser;      (SEQ ID NO:1)

Phe-His-Glu-Phe-Trp-Pro-Thr;      (SEQ ID NO:2)

Phe-His-Ser-Gln-Trp-Pro-Asn;      (SEQ ID NO:3)

Phe-His-Glu-Asn-Trp-Pro;          (SEQ ID NO:4)

Phe-His-Glu-Asn-Trp-Pro-Thr;      (SEQ ID NO:5)

Phe-His-Glu-Gln-Trp-Pro-Ser;      (SEQ ID NO:6)

His-Glu-Asn-Trp-Pro-Ser;          (SEQ ID NO:7)

His-Lys-Asn-Trp-Pro-Ser;          (SEQ ID NO:8)

His-Glu-Asn-Trp-Pro-Ser-Phe       (SEQ ID NO:9)
and

Phe-His-Lys-Pro-Trp-Arg-Ala.      (SEQ ID NO:10)
```

Also comprised within the scope of the present invention are their pharmaceutically acceptable salts, functional fragments of these peptides, peptides that bear a chemical homology with peptides SEQ ID NO: 1-10 and other chemical derivatives of these peptides, provided that they can bind to CD23 molecules.

In another embodiment the peptides and peptidomimetics of the present invention are cyclic. A cyclic peptide or peptidomimetic is defined herein as a peptide or peptidomimetic in which a substituent on one amino acid residue is linked to a substituent on another amino acid residue in the peptide fragment. The linking is either between the side chains of two amino acid residues in the peptide/peptidomimetic, a side chain and the N-terminus of the peptide/peptidomimetic, a side chain and the C-terminus of the peptide/peptidomimetic, or the N-terminus and the C-terminus of the peptide/peptidomimetic. Thus, an amide is bond is formed between the carboxyl group of a residue and the amino group of another residue; ester bonds are formed between the carboxyl group of a residue and the hydroxyl group of a hydroxyl-containing residue; disulfides are formed from amino acid residues containing sulfhydryl groups; and lanthionine bridges are formed by desulfurization of the corresponding disulfide.

The number of atoms in the bridge resulting from the amide, ester, disulfide or lanthionine bond formed as described above will vary depending on the length of side chains and the type of bond (ie, amide, ester, disulfide or lanthionine). The bridge preferably comprises from 2 to 9 atoms, more preferably from 2 to 4 atoms. The most preferred number of atoms contained in the bridge is 4, this bridge preferably comprising an amide bond between the side-chain carboxylic acid of a glutamic acid and an N-terminal residue.

Also included in the scope of the present invention are the pharmaceutically acceptable salts of the peptides according to SEQ ID NO: 1-10, functional (i.e., CD23-binding) fragments of these peptides, peptides that bear a chemical homology with peptides according to SEQ ID NO: 1-10 and functional chemical derivatives of these peptides, especially their analogs is which the C-terminal amino acid is amidated to provide a $CONH_2$ group in place of —COOH.

As used herein, the term salts refers to both salts of a carboxyl group of the peptide chain as well as acid addition salts of an amino group of the polypeptide chain. Salts of a carboxyl group may be formed with either inorganic or organic bases. Inorganic salts include, for example, the alkali metal salts such as the sodium, potassium and lithium salts; the alkaline earth salts such as, for example, the calcium, barium and magnesium salts; and the ammonium, ferrous, ferric, zinc, manganous, aluminium, manganic salts and the like. Salts with organic amines include those formed, for example, with trimethylamine, triethylamine, tri(n-propyl) amine, dicyclohexylamine, triethanolamine, arginine, lysine, histidine, ethylenediamine, glucosamine, methylglucamine, purines, piperazines, piperidines, caffeine, procaine and the like.

Acid addition salts include, for example, salts with mineral acids such as for example hydrochloric acid, hydrobromic acid, sulfuric acid, phosphoric acid, nitric acid and the like; and salts with organic acids such as for example, acetic acid, oxalic acid, tartaric acid, succinic acid, maleic acid, fumaric acid, gluconic acid, citric acid, malic acid, ascorbic acid, benzoic acid and the like.

Functional fragments of the peptides according to the invention are peptides corresponding to SEQ ID NO: 1-10, wherein one or more of the amino acids of SEQ ID NO: 1-10 is deleted, which still retain the ability to bind to. CD23 molecules. Preferred functional fragments of the peptides according to the invention are those in which at most two amino acids are deleted. Even more preferred are those in which only one amino acid is deleted, and particularly $X_1$. Also included in the scope of the present invention, are peptides that are homologues of the peptides according to SEQ ID NO: 1-10. The term homologues as used herein refers to peptides which have amino-acids in common with the sequence according to SEQ ID NO: 1-10 provided that they bind to CD23.

Also included in the scope of the present invention, is an isolated polypeptide comprising an amino acid sequence selected from the group consisting of:
  a) a polypeptide comprising an amino acid sequence of SEQ ID NO: 1-10,
  b) a polypeptide comprising an amino acid sequence at least about 83% identical to an amino acid sequence of SEQ ID NO: 1-10,
  c) a biologically active fragment of a polypeptide having an amino acid sequence of SEQ ID NO: 1-10, and
  d) an immunogenic fragment of a polypeptide having an amino acid sequence of SEQ ID NO: 1-10.

Peptides according to the invention can be chemically synthesised by methods well known in the art, including, for example, solid-phase peptide synthesis. They can also be expressed from a recombinant nucleic acid molecule encoding the peptide. Thus, the invention also provides isolated nucleic acid molecules encoding a peptide corresponding to SEQ ID NO: 1-10 as described above, functional fragments of these peptides, peptides that bear a chemical homology with peptides according to SEQ ID NO: 1-10 and peptides and proteins comprising a peptide sequence according to SEQ ID NO: 1-10.

A peptide according to the invention, which will bind to CD23, can be used in the manufacture of a medicament for the treatment or prophylaxis of disorders mediated by CD23. Such disorders include but are not limited to arthritis, lupus erythematosus, Hashimoto's thyroiditis, multiple sclerosis, diabetes, uveitis, dermatitis, psoriasis, urticaria, nephrotic syndrome, glomerulonephritis, inflammatory bowel disease, ulcerative colitis, celiac disease, Crohn's disease, Sjogren's syndrome, allergies, allergic asthma, intrinsic asthma, acute asthmatic exacerbation, rhinitis, eczema, endometriosis, graft versus host disease (GVH), chronic obstructive pulmonary disease (COPD), insulitis, bronchitis (particularly chronic bronchitis), diabetes (particularly type 1 diabetes), B-CLL and other B-cell malignancies, diseases related to B cell malfunctions, and Parkinson's disease.

Pharmaceutical compositions that contain one or several peptides according to the invention that bind to CD23 are also included in the scope of the present invention. Such pharmaceutical compositions can also comprise other therapeutically active agents, including other anti-inflammatory molecules. The CD23 binding peptide will usually be supplied as part of a sterile, pharmaceutically acceptable composition. This pharmaceutical composition may be in any suitable form, depending upon the desired method of administering it to a patient. The compositions according to the invention can be administered parenterally, for example intravenously, intramuscularly, intra-rectal, intra-vaginal or sub-cutaneously, they can be given orally or nasally by means of a spray, as drops or suppositories. They may be formulated as solutions in water or oil or in emulsions. Formulations that prevent quick peptide degradation are preferred. Such formulations include all forms of encapsulation and are not limited to: microspheres and liposomes. Any appropriate carrier or diluent may be used, provided that it is compatible with the mode of administration and the peptide stability. Excipients include: water, alcohol, polyols, glycerine, vegetable oils, preserving agents, stabilising agents, solubilising agents, wetting agents, emulsifiers, sweeteners, colorants, odourants, salts, buffers, coating agents or antioxidants.

Suitable dosage of the CD23 binding peptide according to the invention will vary, depending upon factors such as the disease or disorder to be treated, the route of administration and the age and weight of the individual to be treated.

It will be appreciated that the actual dosages of the compounds used in the compositions of this invention will vary according to the particular complex being used, the particular composition formulated, the mode of administration and the particular site, host and disease being treated. Optimal dosages for a given set of conditions can be determined by those skilled in the art using conventional methods in view of the experimental data for an agent. For oral administration, an exemplary daily dose generally employed is from about 0.001 to about 1000 mg/kg of body weight, more preferably from about 0.01 to about 100 mg/kg body weight, with courses of treatment repeated at appropriate intervals. Administration of prodrugs are typically dosed at weight levels which are chemically equivalent to the weight levels of the fully active form.

The compositions of the invention may be manufactured using methods generally known for preparing pharmaceutical compositions, e.g., using conventional techniques such as mixing, dissolving, granulating, dragee-making, levigating, emulsifying, encapsulating, entrapping or lyophilizing. Pharmaceutical compositions may be formulated in a conventional manner using one or more physiologically acceptable carriers. The term carrier means a non-toxic material used in the formulation of pharmaceutical compositions to provide a medium, bulk and/or useable form to a pharmaceutical composition. A carrier may comprise one or more of such materials such as an excipient, stabilizer, or an aqueous pH buffered solution. Examples of physiologically acceptable carriers include aqueous or solid buffer ingredients including phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEENT, polyethylene glycol (PEG), and PLURONICST.

The present invention includes within its scope an assay and an assay kit for detecting CD23 in a biological sample, the assay comprising the following steps:
a) treating a sample with a polypeptide of the present invention; and
b) detecting the amount of the polypeptide bound to the sample.

Step (b) above may be facilitated by first removing the unbound polypeptide prior to detection of the bound polypeptide, however, removal of the unbound polypeptide is not a necessary prerequisite to determining the amount of bound polypeptide.

Biological samples include but are not limited to biological fluids, tissue extracts, freshly harvested cells such as B lymphocytes, monocytes/macrophages, eosinophils, platelets, T cells, epithelial cells. Due to the high affinity of the peptides and peptidomimetics to CD23, peptides and peptidomimetics may be used for CD23-detection by ELISA, or serum sCD23 clearance, for example by dialysis over an absorbent column.

The biological sample may be treated with a solid phase support such as nitrocellulose, or other solid support which is capable of immobilizing cells, cell particles or soluble proteins. Well-known supports include glass, polystyrene, polypropylene, polyethylene, dextran, nylon amylases, natural and modified celluloses, polyacrylamides, gabbros and magnetite. The support material may have virtually any possible structural configuration so long as the coupled molecule is capable of binding to a polypeptide. Thus, the support or carrier configuration may be spherical, as in a bead, cylindrical, as in the inside surface of a test tube, or the external surface of a rod. Alternatively, the surface may be flat such as a sheet, test strip, etc. Those skilled in the art will know many other suitable carriers for binding antibody or antigen, or will be able to ascertain the same by use of routine experimentation.

In one embodiment the sample comprises a cell or a cell lysate.

Methods to detect binding can include, for example, the use of labeled CD23-binding peptides or ligands and detection techniques such as solid-phase plate assays; immunoprecipitation; Western blotting, and fluorescence assays. Such technologies are well established and within the technical expertise of one of ordinary skill in the art. A polypeptide is labelled by covalently linking a detectable marker to the polypeptide. Such markers include, but are not limited to fluorescent, biotin, radioactive, and luminescent moieties. In this regard the present invention includes a polypeptide of the present invention wherein the polypeptide is labelled with a detectable marker.

The present invention also includes within its scope a diagnostic test for a condition or disease associated with CD23 in a biological sample comprising the steps of:
 a) combining the biological sample with a polypeptide of the present invention, under conditions suitable for the polypeptide to bind CD23 and form a complex; and
 b) detecting the complex, wherein the presence of the complex correlates with the presence of CD23 in the biological sample.

The present invention also includes an isolated polynucleotide encoding a polypeptide of the present invention. In a preferred embodiment the isolated polynucleotide has a sequence of SEQ ID NO: 11-20:

```
SEQ ID NO: 11   5'-TTT CAT GAG AAT TGG CCT TCG-3'

SEQ ID NO: 12   5'-TTT CAT GAG TTT TGG CCT ACC-3'

SEQ ID NO: 13   5'-TTT CAT TCG CAG TGG CCT AAC-3'

SEQ ID NO: 14   5'-TTT CAT GAG AAT TGG CCT-3'

SEQ ID NO: 15   5'-TTT CAT GAG AAT TGG CCT ACC-3'

SEQ ID NO: 16   5'-TTT CAT GAG CAG TGG CCT TCG-3'

SEQ ID NO: 17   5'-CAT GAG AAT TGG CCT TCG-3'

SEQ ID NO: 18   5'-CAT AAG AAT TGG CCT TCG-3'

SEQ ID NO: 19   5'-CAT GAG AAT TGG CCT TCG TTT-3'

SEQ ID NO: 20   5'-TTT CAT AAG CCT TGG AGG GCC-3'
```

Also included in the scope of the present invention is a polynucleotide sequence comprising a polynucleotide having a sequence complementary to a polynucleotide of SEQ ID NO: 11-20.

SEQ ID NO: 11-20 are representative of nucleic acid sequences that encode for the amino acid sequences of SEQ ID NO: 1-10. It is within the scope of the invention that such nucleic acid sequences can be RNA, DNA, or a hybrid of either. Furthermore, it is well recognized that the genetic code is degenerate, i.e., an amino acid may be coded for by more than one codon. Degenerate codons encode the same amino acid residue, but contain different triplets of nucleotides. Accordingly, for a given polynucleotide sequence encoding an amino acid sequence of the present invention, there will be many degenerate polynucleotide sequences encoding that modulator. These degenerate polynucleotide sequences are considered within the scope of this invention.

In addition, it will also be appreciated by one of skill in the art that different organisms, cells, and cellular compartments may utilize different genetic codes. Thus, a single polynucleotide sequence may encode different polypeptides depending on its cellular context. Accordingly, in addition to the standard genetic code, polypeptides encoded by non-standard genetic codes are also considered within the scope of this invention. These non-standard genetic codes include, but are not limited to, the vertebrate mitochondrial code, the yeast mitochondrial code, the mold, protozoan, and coelenterate mitochondrial code, the mycoplasma/spiroplasma code, the invertebrate mitochondrial code, the ciliate, dasycladacean and hexamita nuclear code, the echinoderm mitochondrial code, the euplotid nuclear code, the bacterial and plant plastid code, the alternative yeast nuclear code, the ascidian mitochondrial code, the flatworm mitochondrial code, blepharisma nuclear code, chlorophycean mitochondrial code, trematode mitochondrial code, scenedesmus obliquus mitochondrial code, and the thraustochytrium mitochondrial code.

Also included in the scope of the present invention is a recombinant polynucleotide comprising a promoter sequence operably linked to a polynucleotide of the present invention. Operably linked means arranged so as to have a functional relationship.

With regard to expression vectors the term operably linked means a desired gene or genes are inserted such that they are appropriately positioned with regard to the signals that control transcription and translation such that they provide for sufficient expression of the gene(s). An expression vector is an artificial DNA sequence, or a naturally-occurring DNA sequence that has been artificially modified, into which desired genes can be inserted and which contains transcription and translation signals that direct the expression of the inserted genes in host cells.

Also included in the scope of the present invention, is a cell transformed with a recombinant polynucleotide of the present invention.

Also included in the scope of the present invention is a transgenic organism comprising a recombinant polynucleotide of the present invention. A transgenic animal is an animal into which has been introduced, by human manipulation, one or more genes not native to the animal.

Also included in the scope of the present invention, is a method for producing a polypeptide of the present invention, the method comprising:
 a) transforming a cell with a recombinant polynucleotide, and the recombinant polynucleotide comprises a promoter sequence operably linked to a polynucleotide encoding a polypeptide of the present invention, and
 b) culturing the cell under conditions suitable for expression of the polypeptide, and
 c) recovering the polypeptide so expressed.

In one embodiment the polypeptide comprises a sequence of SEQ ID NO: 1-10.

The polypeptides of the present invention may be prepared by recombinant technology methods, isolated from natural sources, or prepared synthetically, and may be of prokaryptic or eukaryotic origin. The polypeptides of the present invention may be unglycosylated or modified subsequent to translation. Such modifications include glycosylation, phosphorylation, acetylation, myristoylation, methylation, isoprenylation, and palmitoylation. Glycosylated polypeptides are produced in mammalian cells. Using recombinant DNA technology, the nucleic acid encoding the polypeptide is inserted into a suitable vector, which is inserted into a suitable host cell. The polypeptide produced by the resulting host cell is recovered and purified. The polypeptides are characterized by amino acid composition and sequence, and biological activity.

All patents and publications cited above are herein incorporated by reference.

EXAMPLES

Example 1

Phage Display

Phage display describes a selection technique in which a peptide or protein is expressed as a fusion with a coat protein of a bacteriophage, resulting in display of the fused protein on the exterior surface of the phage virion, while the DNA encoding the fusion resides within the virion. Phage display has been used to create a physical linkage between a vast library of random peptide sequences to the DNA encoding each sequence, allowing rapid identification of peptide ligands for a variety of target molecules (antibodies, enzymes, cell-surface receptors, etc.) by an in vitro selection process called panning. In its simplest form, panning is carried out by incubating a library of phage-displayed peptides with a plate (or bead) coated with the target, washing away the unbound phage, and eluting the specifically-bound phage. (Alternatively the phage can be reacted with the target in solution, followed by affinity capture of the phage-target complexes onto a plate or bead that specifically binds the target.) The eluted phage is then amplified and taken through additional cycles of panning and amplification to successively enrich the pool of phage in favor of the tightest binding sequences. After 3-4 rounds, individual clones are characterized by DNA sequencing and ELISA.

In the present experiments a derivative of wild-type M13 phage (Ph.D.-7™ Phage Display Peptide Library Kit, New England Biolabs, #E8100S) is used. This is a linear 7-mer library which contains $2.0\times10^9$ independent clones.

The library is amplified once such that each panning experiment is carried out using on the order of 100 copies of each sequence in 10 µl of the supplied phage. Simple propagation of the library as phage rather than plasmid eliminates the need for antibiotic selection and a separate helper phage. For phage amplification, the bacteria strain XL1Blue (Stratagene, genotype recA1 endA1 gyrA96 thi-1 hsdR17 supE44 relA1 lac [F'proAB lacµZ ΔM15 Tn10 (Tetr)] is used.

Example 2

CD23 Protein and Quantification

CD23-coding cDNA is obtained from the human B-lymphoblast cell line RPMI 8866. The nucleotide sequence of this cDNA predicts a polypeptide with 321 amino acids and a molecular weight of 36 kD. A functional CD23 capable of binding IgE was expressed in Chinese hamster ovary (CHO) cells (Ludin C et al., EMBO J., 6:109-114 (1987)).

CD23 (2 g) is purified to homogeneity from CHO-transfected cells (kind gift from Novartis, Basel, Switzerland). The presence of CD23 is controlled by a specific ELISA developed using a mouse monoclonal anti-human CD23 antibody (clone 135, IgG$_1$κ isotype). CD23-MoAb (135) is applied on a plastic surface, after reaction with CD23, another anti-CD23-MoAb (clone 25)-FITC is used for CD23 quantification.

Example 3

Phage Selection and CD23 Interaction by "Biopanning"

Purified CD23 protein is applied on sterile polystyrene petri dishes, while carbonate buffer is applied to some dishes as negative control. After washing and surface saturation, $2.0\times10^{11}$ recombinant phages are added to each dish and incubated at room temperature for one hour under gentle agitation. This allows the contact and the fixation of phage-derived peptides to the dish-coated molecules. Subsequent washing permits the elimination of non-binding phages or those with low affinity. After "biopanning", phages are eluted using acid buffer, counted and amplified on bacteria cultures.

Two other biopanning procedures are then applied on eluted phages using CD23-coated dishes. These procedures permit enrichment of the CD23-specific phages.

Following amplification, DNA from each phage clone is extracted and the sequence is determined. Sequencing is performed using automated sequencer Li-cor 4000. The analysis of nucleotide sequences of phages allows the identification and the chemical synthesis of corresponding peptides. Following biopanning, sequencing of the phage reveals the polynucleotide sequence encoding for the amino acid sequence which bound to CD23. for instance, one biopanning procedure identified the following sequence:

5'-TTT CAT GAG AAT TGG CCT TCG-3'    (SEQ ID NO:11)

This sequence encodes for the following amino acid sequence:

Phe His Glu Asn Trp Pro Ser    (SEQ ID NO:1; p30A)

The sequence FHENWPS (SEQ ID NO: 1; p30) is the most frequently selected peptide. The following sequences were selected less frequently:

| FHESWPP | (SEQ ID NO:21; p30B) |
| FHEFWPL | (SEQ ID NO:22; p30C) |
| FHEFWPT | (SEQ ID NO:2; p30D) |
| FHSQWPN | (SEQ ID NO:3; p30E) |
| FHSQWPG | (SEQ D NO:23; p30F) |

FHENWPS (SEQ ID NO: 1; p30A) was selected as the lead CD23-binding compound. Peptides and petidomimetics were synthesized based upon this sequence, including modifications to the peptides, such as cyclicization, and retro-inversal. Table 1 depicts some of these sequences. "Activity" refers to the ability of a particular peptide or peptidomimetic to inhibit binding of anti-CD23-FITC monoclonal antibody to CD23+ cells. Aside from the standard single letter amino acid designations, the following abbreviations are used:

2 Nal=2' napthyl alanine
Tic=tetrahydrolsoquinoline-3-carboxylic acid
4 Indoyl A=4' indolyl alanine
beta W=(S) 3-amino 4-(3-indoyl)butyric acid
cyclo L=1-amino cyclopentane-1-carboxylic acid
beta A=beta alanine
ho Pro=homo proline
tpi=tetrahydronorharman-3-carboxylic acid
cit=citruline
Dap=2,3-diaminoproprionic acid
Thiazoyl=4' thiazoyl alanine
Des Amino H=3-(imadazol-4-yl)proprionic acid
1 Me His=1-N-methyl histidine
Sar=N-methyl glycine
CCpma=1-(amino methyl) cyclopentane-1-carboxylic acid Orn=ornithine
CGG=substrate for fluorescent label
GGC=substrate for fluorescent label
Cyclic H2T=N-terminus amino group to C-terminus carboxyl group linkage
Cyclic H2E=N-terminus amino group to position 6 Glu gamma (side chain) carboxyl group linkage
Cyclic Orn2T=delta (side chain) amino group of ornithine C-terminal carboxyl group linkage
Cyclic E2K=Glu alpha carboxyl group to Lys epsilon (side chain) amino group linkage
Ac=acetyl
E=peptide linkage between Glu and next amino acid occurs through gamma (side chain) carboxyl group of Glu rather than alpha carboxyl group
allyl-=—CH$_2$—CH=CH$_2$
allyl-sidechain metathesis=the reaction of two allyl-groups to form a —CH$_2$—CH=CH—CH$_2$— linkage Lower case letters indicate D-enantiomers of amino acids. For example, the sequence of compound 250, below, is spwneh, which is a retroinverted peptide of compound 244 (HENWPS; SEQ ID NO:7).

TABLE 1

| Compound | 1 | 2 | 3 | 4 | 5 | 6 | 7 | 8 | Comment | Activity |
|---|---|---|---|---|---|---|---|---|---|---|
| 243 | Ac | H | E | N | W | P | S | CONH2 | | +++ |
| 244 | | H | E | N | W | P | S | CONH2 | | +++ |
| 222 | | H | E | N | Tic | P | S | | | ++ |
| 300 | | H | E | N | 4 Indolyl A | P | S | | | ++ |
| 288 | | H | N | E | W | P | S | | | ++ |
| 249 | | H | E | N | W | P | S | CONH$_2$ | | +++ |
| 289 | | H | E | P | W | R | S | | | ++ |
| 283 | | H | E | N | beta W | P | S | | | ++ |
| 281 | | H | P | N | W | R | S | | | +++ |
| 250 | | s | p | w | n | e | h | CONH$_2$ | | +++ |
| 290 | | H | Cys | N | W | Cys | S | | | ++ |
| 306 | | H | E* | N | W | K | S | | cyclic E2K | +++ |
| 333 | | H | E | N | W | K | S | | | +++ |
| 274 | | H | E | N | W | cyclo L | S | | cyclic H2T | ++ |
| 298 | | H | E | N | W | P | S | G | cyclic H2T | ++ |
| 299 | | H | E | N | W | G | S | | cyclic H2T | ++ |
| 327 | | H | E | N | W | E | S | | cyclic H2E | +++ |
| 353 | F | H | E | N | W | E | S | | cyclic H2E | ++ |
| 349 | F | H | E | N | W | P | A | | | +++ |
| 316 | F | H | E | N | W | A | S | | | +++ |
| 329 | F | H | E | N | A | P | S | | | +++ |
| 331 | F | H | E | A | W | P | S | | | ++ |
| 337 | F | H | A | N | W | P | S | | | ++ |
| 338 | F | A | E | N | W | P | S | | | ++ |
| 328 | F | H | E | N | W | beta A | S | | | +++ |
| 330 | F | H | E | N | beta A | P | S | | | ++ |
| 332 | F | H | E | beta A | W | P | S | | | ++ |
| 340 | F | H | beta A | N | W | P | S | | | +++ |
| 339 | F | beta A | E | N | W | P | S | | | +++ |
| 368/369 | F | h | E | N | W | P | S | | | +++ |
| 367 | F | H | E | n | W | P | S | | | ++ |
| 366 | F | H | E | N | w | P | S | | | +++ |
| 334 | F | H | E | N | W | p | S | | | ++ |
| 359 | F | H | E | N | Tpi | P | S | | | ++ |
| 364 | | H | E | Q | W | P | S | | | ++ |
| 384 | | R | E | N | W | P | S | | | +++ |
| 392 | | H | E | N | W | Beta A | S | | cyclic H2T | ++ |
| 398 | | H | E | N | W | Sar | S | | cyclic H2T | ++ |
| 377 | CGG | F | H | E | N | W | P | S | Fluor | ++ |
| 400 | | H | Q | N | W | P | S | CONH$_2$ | | ++ |
| 405 | | H | E | Q | W | cyclo L | S | | | ++ |
| 397 | S | P | W | N | E | H | F | | scrambled | ++ |
| 420 A | | H | E | N | W | cCpma | S | | cyclic H2T | +++ |
| 411 | | | Ac | N | W | CO$_2$H | | | | +++ |
| 409 | | | Ac | N | W | G | CO$_2$H | | | +++ |
| 410 | | | Ac | N | W | Beta A | CO$_2$H | | | +++ |
| 435A | | H | C | N | W | C | E | | cyclic H2T & disulfide (1st diastereomer) | +++ |
| 435B | | H | C | N | W | C | E | | cyclic H2T & disulfide (2nd diastereomer) | +++ |
| 436 | | H | E | N | A | P | S | | same as 329 | +++ |
| 437 | | H | E | N | W | S | | | cyclic H2T | +++ |
| 440 | | H | E | N | W | Orn | S | | cyclic Orn2T | +++ |
| 489 | | NH$_2$ | G[allyl-] | N | W | G[allyl-] | | | cyclic: allyl-sidechain metathesis | +++ |

TABLE 1-continued

| Compound | 1 | 2 | 3 | 4 | 5 | 6 | 7 | 8 | Comment | Activity |
|---|---|---|---|---|---|---|---|---|---|---|
| 490 | | | G[allyl-] | N | W | G[allyl-] | S | | bicyclic: allyl-sidechain metathesis & cyclic H2T | +++ |
| 491 | | | Ac | w | n | CO$_2$H | | | D amino retro inverso | ++++ |
| 492 | | | Ac | n | w | CO$_2$H | | | D amino inverso | ++ |

Example 4

Cell Cultures

Monocytes are isolated from normal human peripheral blood. Samples are collected from normal volunteers (20-50 years) by blood bank. They are all tested for the absence of HIV or HBV contaminations prior to use. Human normal mononuclear cells are obtained by Ficoll (Histopaque, Sigma) gradient separation of peripheral blood leukocytes. Monocytes are separated from lymphocytes by adherence to plastic dishes coated with fetal calf serum (FCS) as described (Vouldoukis I., et al., Proc. Natl. Acad. Sci. USA., 92: 7804-7808 1995). Following this procedure, >90% of cells express CD14 antigen and display cytochemical characteristics of monocytes. The cells are then incubated in DMEM supplemented with L-non-essential amino acids, sodium pyruvate, glutamine, penicillin, streptomycin, and 10% FCS (all from Gibco Laboratories, Grand Island, N.Y.). Above culture medium, chemicals, and FCS are tested for the absence of direct activation effect on human monocytes (CD23 expression and TNF-α production as activation markers). Following 24-48 hr adherence to culture flasks, these cells differentiate into macrophage-like cells displaying non-specific esterase activity that is inhibited by sodium fluoride.

Normal human donor-derived adherent cells have low if any surface CD23 expression and are designated in the present work as macrophages. CD23 expression is obtained following cell incubation with recombinant human interleukin 4 (long/ml). In patients with inflammatory diseases (e.g., Arthritis), peripheral blood-derived monocytes may yet express CD23 and do not require IL-4. Tissue-derived macrophages are mostly CD23$^+$.

For some experiments, EBV-transformed, CD23$^+$ human B-cell lines are used for CD23-binding assay. These cells are not appropriate for a functional assay as B lymphocytes lack the inflammatory mediators of macrophages.

Example 5

Activation of Inflammatory Response in Human Macrophages

Monocyte-derived macrophages (CD23$^+$) are activated through the cross-linking of their CD23 surface molecules by appropriate MoAb (20 µg/ml, clone 135, IgG$_1$κ isotype) or by human IgE/anti-IgE complexes (IgE, Stallergene, Paris, France; goat anti-human-IgE, Nordic Immunology, Tilburg, The Netherlands). This activation pathway promotes the activation of iNOS mRNA transcription and the generation, by macrophages, of various inflammatory mediators such as nitric oxide (NO), TNF-α, reactive oxygen radicals, IL-1, and IL-6 (for, a review see: Dugas B, et al., Immunol Today, 16:574-580(1995)).

Example 6

Quantification of Inflammatory Response

Following 1-3 day incubation at 37° C., 5% CO$_2$ in humid atmosphere, macrophages are analyzed for their inflammatory response as following:
  24 hr incubation: Detection of iNOS-mRNA by RT-PCR;
  36-48 hr incubation: Detection of intracellular NO by diaminofluorescein diacetate (DAF) fluorescent detector;
  48-96 hr incubation: Collection of supernatants for the detection of cytokines and nitrites. Nitrites are quantified by Greiss method (Davies et al., Methods in Molecular Biology, 225:305-320, 2003) while IL-1, IL-6 and TNF-α were quantified using commercial ELISA kits. The following antibodies and reagents were utilized:
  Recombinant human IL-4 (a gift from Schering Plough, Dardilly, France);
  human IgE (Stallergene, Paris, France);
  goat anti-human-IgE (Nordic Immunology, Tilburg, The Netherlands);
  L-NIL (SNAP, Alexis Corporation, Laufelfingen, Switzerland),
  fetal calf serum (FCS) (all from Gibco Laboratories, Grand Island, N.Y.)
  CD23-MoAb (clone 25) (Immunotech, Marseille Lumigny, France).

Following quantitation of nitrites, a percentage inhibition relative to controls is calculated. The following results demonstrating inhibition of iNOS production were obtained:

TABLE 2

| Name | Sequence | % Inhibition |
|---|---|---|
| 491 | Ac w n CO$_2$H | 94 |
| 411 | Ac N W CO$_2$H | 84 |
| 490 | G[allyl-] N W G[allyl-] S | 81 |
| P30L | F H E N W P | 78 |
| 492 | Ac n w CO$_2$H | 77 |
| P30M | F H E N W P T | 76 |
| p30A | F H E N W P S | 74 |
| 398 | H E N W Sar S | 74 |
| 299 | H E N W G S | 74 |
| P30K | H E N W P S | 74 |
| P30O | F H E Q W P S | 73 |
| 333 | H E N W K S | 69 |
| p30D | F H E F W P T | 68 |
| p30E | F H S Q W P N | 65 |
| 489 | NH$_2$ G[allyl-] N W G[allyl-] | 62 |
| 410 | Ac N W BetaA CO$_2$H | 61 |
| 436 | H E N A P S | 60 |

TABLE 2-continued

| Name | Sequence | % Inhibition |
|------|----------|--------------|
| 327 | H E N W E S | 60 |
| 437 | H E N W S | 56 |
| P30G | F H K P W R A | 55 |
| 331 | F H E A W P S | 43 |
| 328 | F H E N W betaA S | 26 |

Example 7

Analysis of CD23-Specific Binding

Three methods are used to assay the ability of various compounds to block CD23 recognition by specific MoAb or IgE/anti-IgE immune complexes:
 a) inhibition of the binding to CD23 coated surfaces: detected by ELISA method;
 b) inhibition of anti-CD23-FITC binding to CD23+ cells (Macrophages or B-cell lines);
 c) inhibition of IgE/anti-IgE-FITC binding to CD23+ cells.

Coated surface or cells are incubated with CD23-counterstructures for 1-4 hrs prior to the addition of FITC-conjugated ligands.

For inflammatory functions, cells are pre-incubated with CD23-counterstructures during 4 hours prior to their incubation with CD23-MoAb or IgE/anti-IgE complexes. Cell supernatants are collected 2-4 days later and tested for their contents in various mediators.

(Below are the results of biological activities followed by the analysis of various peptide testing)

1. Blockade of CD23 Binding by Specific Peptides $CD23^+$ cells are incubated in the presence of inhibitory peptide (p30A) or unrelated control peptide (pNu). Fluorescence intensity was quantified by cytofluorometer. Below are the percentages of fluorescence intensity recovered following cell pre-incubation with CD23-peptide or control peptides, compared to cells incubated in medium alone.

|  | CD23-Ab | p30A + CD23-Ab | pNu + CD23-Ab |
|--|---------|----------------|---------------|
| Experiment 1 | 100% | 40% | 120% |
| Experiment 2 | 100% | 56% | 88% |
| Experiment 3 | 100% | 10% | 94% |

Similar data were obtained with the use of IgE/anti-IgE-FITC as CD23 ligand.

|  | IgE/Anti-IgE-FITC | p30A + IgE/Anti-IgE-FITC | pNu + IgE/Anti-IgE-FITC |
|--|-------------------|--------------------------|-------------------------|
| Experiment 1 | 100% | 23% | 73% |
| Experiment 2 | 100% | 61% | 110% |

2. Inhibition of NO Generation from Activated Macrophages by Specific Peptides

Inflammatory responses of human macrophages almost correlated with in vivo generation of nitric oxide by these cells. We use this inflammatory mediator as a marker of cell activation.

$CD23^+$ cells are incubated in the presence or the absence of an inhibitory peptide (p30A) for 4 hours. CD23-MoAb or IgE/anti-IgE immune complexes are added. Following 3-5 day incubation, cell supernatants are harvested and the level of nitrites quantified by Greiss reaction (Davies et al., Methods in Molecular Biology, 225:305-320, 2003).

|  | None | CD23-Ab | p30A + CD23-Ab | IgE/anti-IgE | p30A + IgE/anti-Ig |
|--|------|---------|----------------|--------------|--------------------|
| Experiment 1 | 3.2* | 14.4 | 7.5 | 9.3 | 2.6 |
| Experiment 2 | 0.9 | 4.5 | 1.2 | 2.8 | 1.4 |

*µM of [NO$_2$—]

The effect of CD23-Peptide or a negative control on inflammatory functions of macrophages derived from synovial fluid of patients with Rheumatoid Arthritis is also investigated.

|  | None | CD23-Ab | p30A | p30A + CD23-Ab | pNu + CD23-Ab |
|--|------|---------|------|----------------|---------------|
| Experiment 1 | 8.3* | 16.8 | 8.5 | 7.9 | 15.2 |
| Experiment 2 | 9.5 | 18.9 | 10.3 | 9.5 | 14.4 |

*µM of [NO2-]

NO production from rat peritoneal macrophages and rat peripheral macrophages is also determined. Peritoneal macrophages are highly $CD23^+$ and produce much higher quantities of pro-inflammatory mediators compared to peripheral blood-derived cells. $CD23^+$ cells are incubated in the presence or the absence of an inhibitory peptide (p30A) for 4 hours. IgE/DNP-BSA is added to induce CD23 cross-linking. L-NIL is a specific inhibitor of NOS-II. Pep– is a negative control peptide. Following 3-5 day incubation, cell supernatants are harvested and the level of nitrites quantified by Greiss reaction (Davies et al., Methods in Molecular Biology, 225:305-320, 2003). FIG. 2 shows that the addition of p30A inhibits IgE/DNP-BSA-induced NO production by macrophages.

3. Inhibition of TNF-α Generation from Activated Macrophages by Specific Peptides In addition to NO, the effect of peptides on the production of TNF-α, a well-documented effector factor during inflammatory diseases, is also tested.

$CD23^+$ cells are incubated in the presence or the absence of an inhibitory peptide (p30A) for 4 hours. CD23-MoAb or IgE/anti-IgE immune complexes are added. Following 3-5 day incubation, cell supernatants are harvested and the level of TNF-α, quantified by specific ELISA.

|  | None | CD23-Ab | p30A + CD23-Ab | % Inhibition | pNu + CD23-Ab |
|--|------|---------|----------------|--------------|---------------|
| Experiment 1 | <10* | 144 | 77 | 47 | 162 |
| Experiment 2 | <10 | 193 | 89 | 54 | 132 |

*pg TNF-α/ml

The effect of CD23-Peptide or a negative control on inflammatory functions of macrophages derived from peripheral blood or the synovial fluid of patients with Rheumatoid Arthritis is also investigated.

|  | None | CD23-Ab | p30A + CD23-Ab | % Inhibition |
|---|---|---|---|---|
| SF Macrophages | 110* | 235 | 140 | 41 |
| Peripheral Macrophages | 39 | 145 | 40 | 73 |

*pg TNF-α/ml

4. Treatment of Arthritic Rats

On day 0, 6-week old female Lewis rats weighing 145-155 g are injected subcutaneously with an arthritis-inducing emulsion. The rats are injected with 300 µl of the emulsion which contains:

- 2 mg/rat heat-inactivated *Mycobacterium butyricum* diluted into;
- 240 µl of Vaseline;
- 30 µl of Tween-20; and
- 30 µl of PBS.

The immunization step is repeated on day 7. The rats present arthritis signs by days 15 have to 21. Arthritic signs are assigned a clinical score (1-4). By day 40, the clinical scores increase from 1 to 3 or 4. Slower weight progression is also observed in immunized rats (FIG. 1a).

Unique injection (intraperitoneal or subcutaneous) of the inhibitory peptide p30A at day 0 has no affect on arthritis appearance. However, subcutaneous injection of 5 mg of p30A after the appearance of clinical signs results in complete remission of arthritic symptoms for 50% of the rats (FIG. 1b) as well as decreased clinical scores in 25% of the remaining rats.

The results using subcutaneous injection of p30A are in contrast to results obtained using intraperitoneal injection or intravenous treatment, which do not induce remission of the arthritic condition.

Example 8

In Vivo Prevention and Treatment of Rats with p30A

To demonstrate preventive efficacy, rats are simultaneously treated to immunization. In addition, to demonstrate therapeutic efficacy, another group of rats is simultaneously treated on the first day of the appearance of clinical symptoms following immunization. Each group of animals comprises eight rats. Female Lewis rats (Janvier, Le Genest St Isle, France) are housed under standard laboratory conditions and the animals are allowed free access to food and water. The temperature is kept at 22±2° C. and a 12-hour light/dark schedule is maintained. All animal procedures are performed in strict accordance with the guidelines issued by the European Economic Community "86/609". Adjuvant arthritis (AA) is induced in six weeks-old animals by subcutaneous injection at the base of the tail of 300 µl (1.8 mg) of inactivated *Mycobacterium butyricum* (Difco Laboratories, Detroit, Mich.) diluted in emulsion of 8 ml Vaseline, 1 ml polysorbate 80, and 1 ml PBS (Phosphate Buffer Saline, BioWhittaker, Walkersville, Md.). Rats are boosted one week later with the same dose of antigen and observed for up to 50 days following immunization for clinical symptoms of arthritis. Evaluation of AA severity is performed by two independent observers with no knowledge of the treatment protocol. The severity of AA in each paw is quantified daily by a clinical score measurement from 0 to 2 as following: no signs of inflammation (0); swelling alone (>2 fold paw diameter) (0.5) or swelling/immobility (1.0) of one paw; swelling (1,5) or swelling/immobility (2,0) of two paws. Weight evolution of the animals is measured daily. Rats are injected with peptides or peptidomimetics (dissolved in 0.1% DMSO) I.C. every two days (day 0, 2, 4, 6, and 8) during the initiation of inflammation (preventive) or following the appearance of the inflammatory signs. As negative control, rats are injected with saline.

Clinical scores are determined as described above, and the cumulative clinical score is plotted against days post-immunization (FIGS. 2, 3, and 4).

In each of FIGS. 2, 3, and 4, arrows below the x-axis indicate the days on which IC injections were administered. As shown in FIG. 2, rats treated with p30A in two different dosage regimes show clearly superior clinical scores compared to control rats, consistent with a preventive effect of p30A. As shown in FIG. 3, rats treated with p30A on the day of symptoms first appearing show a clear therapeutic effect at 3 different dosage regimes, versus control rats which did not receive the p30A treatment. As shown in FIG. 4, p30A administration to rats with arthritic symptoms produced weight gain over those rats which did not receive such treatment, and such weight gain approached that of the control rats without arthritic symptoms.

We claim:
1. A CD23-binding peptide, wherein said peptide consists of:
Phe-His-Glu-Phe-Trp-Pro-Thr (SEQ ID NO:2);
Phe-His-Ser-Gln-Trp-Pro-Asn (SEQ ID NO:3);
Phe-His-Glu-Asn-Trp-Pro-Thr (SEQ ID NO:5);
Phe-His-Glu-Gln-Trp-Pro-Ser (SEQ ID NO:6);
His-Glu-Asn-Trp-Pro-Ser (SEQ ID NO:7);
His-Lys-Asn-Trp-Pro-Ser (SEQ ID NO:8);
His-Glu-Asn-Trp-Pro-Ser-Phe (SEQ ID NO:9);
Phe-His-Lys-Pro-Trp-Arg-Ala (SEQ ID NO:10);
His-Glu-Asn-Trp-Lys-Ser (SEQ ID NO:31);
His-Glu-Asn-Trp-Xaa-Ser (SEQ ID NO:32);
His-Glu-Asn-Trp-Gly-Ser (SEQ ID NO:34);
His-Glu-Asn-Trp-Glu-Ser (SEQ ID NO:35);
Phe-His-Glu-Ala-Trp-Pro-Ser (SEQ ID NO:40);
Phe-His-Glu-Asn-Trp-Xaa-Ser (SEQ ID NO:43);
His-Glu-Asn-Ala-Pro-Ser (SEQ ID NO:53);
His-Glu-Asn-Trp-Ser (SEQ ID NO:54);
G[allyl-] N W G[allyl-] (SEQ ID NO:55);
$NH_2$G[allyl-] N W G[allyl-] (SEQ ID NO:56);
Ac wn $CO_2$H
Ac NW $CO_2$H
Ac n w $CO_2$H
Ac N W BetaA $CO_2$H or
H E N W P $CONH_2$ (SEQ ID NO:61).

2. The peptide according to claim 1 wherein at least one amino acid is a D-isomer, an acylated N-terminus, an acetylated N-terminus or amidated C-terminus.

3. A labeled peptide wherein the peptide of claim 1 is labeled with a detectable marker.

4. The peptide according to claim 1 having a specific binding activity to CD23 of $K_d$=being less than $10^{-6}$ M.

5. The peptide according to claim 4 wherein said peptide has a specific binding activity to CD23 of $K_d$ which is between $10^{-6}$ and $10^{-11}$ M.

* * * * *

SEQUENCE LISTING

```
<160> NUMBER OF SEQ ID NOS: 61

<210> SEQ ID NO 1
<211> LENGTH: 7
<212> TYPE: PRT
<213> ORGANISM: Artificial
<220> FEATURE:
<223> OTHER INFORMATION: CD23 binding peptide

<400> SEQUENCE: 1

Phe His Glu Asn Trp Pro Ser
1               5

<210> SEQ ID NO 2
<211> LENGTH: 7
<212> TYPE: PRT
<213> ORGANISM: Artificial
<220> FEATURE:
<223> OTHER INFORMATION: CD23 binding peptide
```

```
<400> SEQUENCE: 2

Phe His Glu Phe Trp Pro Thr
1               5

<210> SEQ ID NO 3
<211> LENGTH: 7
<212> TYPE: PRT
<213> ORGANISM: Artificial
<220> FEATURE:
<223> OTHER INFORMATION: CD23 binding peptide

<400> SEQUENCE: 3

Phe His Ser Gln Trp Pro Asn
1               5

<210> SEQ ID NO 4
<211> LENGTH: 6
<212> TYPE: PRT
<213> ORGANISM: Artificial
<220> FEATURE:
<223> OTHER INFORMATION: CD23 binding peptide

<400> SEQUENCE: 4

Phe His Glu Asn Trp Pro
1               5

<210> SEQ ID NO 5
<211> LENGTH: 7
<212> TYPE: PRT
<213> ORGANISM: Artificial
<220> FEATURE:
<223> OTHER INFORMATION: CD23 binding peptide

<400> SEQUENCE: 5

Phe His Glu Asn Trp Pro Thr
1               5

<210> SEQ ID NO 6
<211> LENGTH: 7
<212> TYPE: PRT
<213> ORGANISM: Artificial
<220> FEATURE:
<223> OTHER INFORMATION: CD23 binding peptide

<400> SEQUENCE: 6

Phe His Glu Gln Trp Pro Ser
1               5

<210> SEQ ID NO 7
<211> LENGTH: 6
<212> TYPE: PRT
<213> ORGANISM: Artificial
<220> FEATURE:
<223> OTHER INFORMATION: CD23 binding peptide

<400> SEQUENCE: 7

His Glu Asn Trp Pro Ser
1               5

<210> SEQ ID NO 8
<211> LENGTH: 6
<212> TYPE: PRT
<213> ORGANISM: Artificial
<220> FEATURE:
<223> OTHER INFORMATION: CD23 binding peptide

<400> SEQUENCE: 8
```

```
His Lys Asn Trp Pro Ser
1               5

<210> SEQ ID NO 9
<211> LENGTH: 7
<212> TYPE: PRT
<213> ORGANISM: Artificial
<220> FEATURE:
<223> OTHER INFORMATION: CD23 binding peptide

<400> SEQUENCE: 9

His Glu Asn Trp Pro Ser Phe
1               5

<210> SEQ ID NO 10
<211> LENGTH: 7
<212> TYPE: PRT
<213> ORGANISM: Artificial
<220> FEATURE:
<223> OTHER INFORMATION: CD23 binding peptide

<400> SEQUENCE: 10

Phe His Lys Pro Trp Arg Ala
1               5

<210> SEQ ID NO 11
<211> LENGTH: 21
<212> TYPE: DNA
<213> ORGANISM: Artificial
<220> FEATURE:
<223> OTHER INFORMATION: nucleotide sequence encoding CD23 binding
      peptide

<400> SEQUENCE: 11
tttcatgaga attggccttc g                                              21

<210> SEQ ID NO 12
<211> LENGTH: 21
<212> TYPE: DNA
<213> ORGANISM: Artificial
<220> FEATURE:
<223> OTHER INFORMATION: nucleotide sequence encoding CD23 binding
      peptide

<400> SEQUENCE: 12
tttcatgagt tttggcctac c                                              21

<210> SEQ ID NO 13
<211> LENGTH: 21
<212> TYPE: DNA
<213> ORGANISM: Artificial
<220> FEATURE:
<223> OTHER INFORMATION: nucleotide sequence encoding CD23 binding
      peptide

<400> SEQUENCE: 13
tttcattcgc agtggcctaa c                                              21

<210> SEQ ID NO 14
<211> LENGTH: 18
<212> TYPE: DNA
<213> ORGANISM: Artificial
<220> FEATURE:
<223> OTHER INFORMATION: nucleotide sequence encoding CD23 binding
      peptide

<400> SEQUENCE: 14
```

```
tttcatgaga attggcct                                                       18

<210> SEQ ID NO 15
<211> LENGTH: 21
<212> TYPE: DNA
<213> ORGANISM: Artificial
<220> FEATURE:
<223> OTHER INFORMATION: nucleotide sequence encoding CD23 binding
      peptide

<400> SEQUENCE: 15
tttcatgaga attggcctac c                                                   21

<210> SEQ ID NO 16
<211> LENGTH: 21
<212> TYPE: DNA
<213> ORGANISM: Artificial
<220> FEATURE:
<223> OTHER INFORMATION: nucleotide sequence encoding CD23 binding
      peptide

<400> SEQUENCE: 16
tttcatgagc agtggccttc g                                                   21

<210> SEQ ID NO 17
<211> LENGTH: 18
<212> TYPE: DNA
<213> ORGANISM: Artificial
<220> FEATURE:
<223> OTHER INFORMATION: nucleotide sequence encoding CD23 binding
      peptide

<400> SEQUENCE: 17
catgagaatt ggccttcg                                                       18

<210> SEQ ID NO 18
<211> LENGTH: 18
<212> TYPE: DNA
<213> ORGANISM: Artificial
<220> FEATURE:
<223> OTHER INFORMATION: nucleotide sequence encoding CD23 binding
      peptide

<400> SEQUENCE: 18
cataagaatt ggccttcg                                                       18

<210> SEQ ID NO 19
<211> LENGTH: 21
<212> TYPE: DNA
<213> ORGANISM: Artificial
<220> FEATURE:
<223> OTHER INFORMATION: nucleotide sequence encoding CD23 binding
      peptide

<400> SEQUENCE: 19
catgagaatt ggccttcgtt t                                                   21

<210> SEQ ID NO 20
<211> LENGTH: 21
<212> TYPE: DNA
<213> ORGANISM: Artificial
<220> FEATURE:
<223> OTHER INFORMATION: nucleotide sequence encoding CD23 binding
      peptide

<400> SEQUENCE: 20
tttcataagc cttggagggc c                                                   21
```

```
<210> SEQ ID NO 21
<211> LENGTH: 7
<212> TYPE: PRT
<213> ORGANISM: Artificial
<220> FEATURE:
<223> OTHER INFORMATION: CD23 binding peptide

<400> SEQUENCE: 21

Phe His Glu Ser Trp Pro Pro
1               5

<210> SEQ ID NO 22
<211> LENGTH: 7
<212> TYPE: PRT
<213> ORGANISM: Artificial
<220> FEATURE:
<223> OTHER INFORMATION: CD23 binding peptide

<400> SEQUENCE: 22

Phe His Glu Phe Trp Pro Leu
1               5

<210> SEQ ID NO 23
<211> LENGTH: 7
<212> TYPE: PRT
<213> ORGANISM: Artificial
<220> FEATURE:
<223> OTHER INFORMATION: CD23 binding peptide

<400> SEQUENCE: 23

Phe His Ser Gln Trp Pro Gly
1               5

<210> SEQ ID NO 24
<211> LENGTH: 6
<212> TYPE: PRT
<213> ORGANISM: Artificial
<220> FEATURE:
<223> OTHER INFORMATION: CD23 binding peptide
<220> FEATURE:
<221> NAME/KEY: misc_feature
<222> LOCATION: (4)..(4)
<223> OTHER INFORMATION: Xaa can be tetrahydrolsoquinoline-3-carboxylic
      acid, 4' indolyl alanine, or beta tryptophan

<400> SEQUENCE: 24

His Glu Asn Xaa Pro Ser
1               5

<210> SEQ ID NO 25
<211> LENGTH: 6
<212> TYPE: PRT
<213> ORGANISM: Artificial
<220> FEATURE:
<223> OTHER INFORMATION: CD23 binding peptide

<400> SEQUENCE: 25

His Asn Glu Trp Pro Ser
1               5

<210> SEQ ID NO 26
<211> LENGTH: 5
<212> TYPE: PRT
<213> ORGANISM: Artificial
<220> FEATURE:
<223> OTHER INFORMATION: CD23 binding peptide

<400> SEQUENCE: 26
```

```
His Glu Asn Trp Pro
1               5

<210> SEQ ID NO 27
<211> LENGTH: 6
<212> TYPE: PRT
<213> ORGANISM: Artificial
<220> FEATURE:
<223> OTHER INFORMATION: CD23 binding peptide

<400> SEQUENCE: 27

His Glu Pro Trp Arg Ser
1               5

<210> SEQ ID NO 28
<211> LENGTH: 6
<212> TYPE: PRT
<213> ORGANISM: Artificial
<220> FEATURE:
<223> OTHER INFORMATION: CD23 binding peptide

<400> SEQUENCE: 28

His Pro Asn Trp Arg Ser
1               5

<210> SEQ ID NO 29
<211> LENGTH: 6
<212> TYPE: PRT
<213> ORGANISM: Artificial
<220> FEATURE:
<223> OTHER INFORMATION: CD23 binding peptide; all amino acids are
      D-form

<400> SEQUENCE: 29

Ser Pro Trp Asn Glu His
1               5

<210> SEQ ID NO 30
<211> LENGTH: 6
<212> TYPE: PRT
<213> ORGANISM: Artificial
<220> FEATURE:
<223> OTHER INFORMATION: CD23 binding peptide

<400> SEQUENCE: 30

His Cys Asn Trp Cys Ser
1               5

<210> SEQ ID NO 31
<211> LENGTH: 6
<212> TYPE: PRT
<213> ORGANISM: Artificial
<220> FEATURE:
<223> OTHER INFORMATION: CD23 binding peptide

<400> SEQUENCE: 31

His Glu Asn Trp Lys Ser
1               5

<210> SEQ ID NO 32
<211> LENGTH: 6
<212> TYPE: PRT
<213> ORGANISM: Artificial
<220> FEATURE:
<223> OTHER INFORMATION: CD23 binding peptide
<220> FEATURE:
<221> NAME/KEY: misc_feature
<222> LOCATION: (5)..(5)
<223> OTHER INFORMATION: Xaa can be 1-amino cyclopentane-1-carboxylic
```

```
      acid, beta alanine, N-methyl glycine, or 1-(amino methyl)
      cyclopentane-1-carboxylic acid

<400> SEQUENCE: 32

His Glu Asn Trp Xaa Ser
1               5

<210> SEQ ID NO 33
<211> LENGTH: 7
<212> TYPE: PRT
<213> ORGANISM: Artificial
<220> FEATURE:
<223> OTHER INFORMATION: CD23 binding peptide

<400> SEQUENCE: 33

His Glu Asn Trp Pro Ser Gly
1               5

<210> SEQ ID NO 34
<211> LENGTH: 6
<212> TYPE: PRT
<213> ORGANISM: Artificial
<220> FEATURE:
<223> OTHER INFORMATION: CD23 binding peptide

<400> SEQUENCE: 34

His Glu Asn Trp Gly Ser
1               5

<210> SEQ ID NO 35
<211> LENGTH: 6
<212> TYPE: PRT
<213> ORGANISM: Artificial
<220> FEATURE:
<223> OTHER INFORMATION: CD23 binding peptide

<400> SEQUENCE: 35

His Glu Asn Trp Glu Ser
1               5

<210> SEQ ID NO 36
<211> LENGTH: 7
<212> TYPE: PRT
<213> ORGANISM: Artificial
<220> FEATURE:
<223> OTHER INFORMATION: CD23 binding peptide

<400> SEQUENCE: 36

Phe His Glu Asn Trp Glu Ser
1               5

<210> SEQ ID NO 37
<211> LENGTH: 7
<212> TYPE: PRT
<213> ORGANISM: Artificial
<220> FEATURE:
<223> OTHER INFORMATION: CD23 binding peptide

<400> SEQUENCE: 37

Phe His Glu Asn Trp Pro Ala
1               5

<210> SEQ ID NO 38
<211> LENGTH: 7
<212> TYPE: PRT
<213> ORGANISM: Artificial
<220> FEATURE:
<223> OTHER INFORMATION: CD23 binding peptide
```

-continued

<400> SEQUENCE: 38

Phe His Glu Asn Trp Ala Ser
1               5

<210> SEQ ID NO 39
<211> LENGTH: 7
<212> TYPE: PRT
<213> ORGANISM: Artificial
<220> FEATURE:
<223> OTHER INFORMATION: CD23 binding peptide

<400> SEQUENCE: 39

Phe His Glu Asn Ala Pro Ser
1               5

<210> SEQ ID NO 40
<211> LENGTH: 7
<212> TYPE: PRT
<213> ORGANISM: Artificial
<220> FEATURE:
<223> OTHER INFORMATION: CD23 binding peptide

<400> SEQUENCE: 40

Phe His Glu Ala Trp Pro Ser
1               5

<210> SEQ ID NO 41
<211> LENGTH: 7
<212> TYPE: PRT
<213> ORGANISM: Artificial
<220> FEATURE:
<223> OTHER INFORMATION: CD23 binding peptide

<400> SEQUENCE: 41

Phe His Ala Asn Trp Pro Ser
1               5

<210> SEQ ID NO 42
<211> LENGTH: 7
<212> TYPE: PRT
<213> ORGANISM: Artificial
<220> FEATURE:
<223> OTHER INFORMATION: CD23 binding peptide

<400> SEQUENCE: 42

Phe Ala Glu Asn Trp Pro Ser
1               5

<210> SEQ ID NO 43
<211> LENGTH: 7
<212> TYPE: PRT
<213> ORGANISM: Artificial
<220> FEATURE:
<223> OTHER INFORMATION: CD23 binding peptide
<220> FEATURE:
<221> NAME/KEY: misc_feature
<222> LOCATION: (6)..(6)
<223> OTHER INFORMATION: Xaa can be beta alanine or the D-form of
      proline

<400> SEQUENCE: 43

Phe His Glu Asn Trp Xaa Ser
1               5

<210> SEQ ID NO 44
<211> LENGTH: 6
<212> TYPE: PRT

```
<213> ORGANISM: Artificial
<220> FEATURE:
<223> OTHER INFORMATION: CD23 binding peptide
<220> FEATURE:
<221> NAME/KEY: misc_feature
<222> LOCATION: (5)..(5)
<223> OTHER INFORMATION: Xaa can be beta alanine, the D-form of
      tryptophan, or tetrahydronorharman-3-carboxylic acid

<400> SEQUENCE: 44

Phe His Glu Asn Xaa Ser
1               5

<210> SEQ ID NO 45
<211> LENGTH: 7
<212> TYPE: PRT
<213> ORGANISM: Artificial
<220> FEATURE:
<223> OTHER INFORMATION: CD23 binding peptide
<220> FEATURE:
<221> NAME/KEY: misc_feature
<222> LOCATION: (4)..(4)
<223> OTHER INFORMATION: Xaa can be beta alanine or the D-form of
      asparagine

<400> SEQUENCE: 45

Phe His Glu Xaa Trp Pro Ser
1               5

<210> SEQ ID NO 46
<211> LENGTH: 7
<212> TYPE: PRT
<213> ORGANISM: Artificial
<220> FEATURE:
<223> OTHER INFORMATION: CD23 binding peptide
<220> FEATURE:
<221> NAME/KEY: misc_feature
<222> LOCATION: (3)..(3)
<223> OTHER INFORMATION: Xaa is beta alanine

<400> SEQUENCE: 46

Phe His Xaa Asn Trp Pro Ser
1               5

<210> SEQ ID NO 47
<211> LENGTH: 7
<212> TYPE: PRT
<213> ORGANISM: Artificial
<220> FEATURE:
<223> OTHER INFORMATION: CD23 binding peptide
<220> FEATURE:
<221> NAME/KEY: misc_feature
<222> LOCATION: (2)..(2)
<223> OTHER INFORMATION: Xaa can be beta alanine or the D-form of
      histidine

<400> SEQUENCE: 47

Phe Xaa Glu Asn Trp Pro Ser
1               5

<210> SEQ ID NO 48
<211> LENGTH: 6
<212> TYPE: PRT
<213> ORGANISM: Artificial
<220> FEATURE:
<223> OTHER INFORMATION: CD23 binding peptide

<400> SEQUENCE: 48

His Glu Gln Trp Pro Ser
1               5
```

```
<210> SEQ ID NO 49
<211> LENGTH: 6
<212> TYPE: PRT
<213> ORGANISM: Artificial
<220> FEATURE:
<223> OTHER INFORMATION: CD23 binding peptide

<400> SEQUENCE: 49

Arg Glu Asn Trp Pro Ser
1               5

<210> SEQ ID NO 50
<211> LENGTH: 6
<212> TYPE: PRT
<213> ORGANISM: Artificial
<220> FEATURE:
<223> OTHER INFORMATION: CD23 binding peptide

<400> SEQUENCE: 50

His Gln Asn Trp Pro Ser
1               5

<210> SEQ ID NO 51
<211> LENGTH: 6
<212> TYPE: PRT
<213> ORGANISM: Artificial
<220> FEATURE:
<223> OTHER INFORMATION: CD23 binding peptide
<220> FEATURE:
<221> NAME/KEY: misc_feature
<222> LOCATION: (5)..(5)
<223> OTHER INFORMATION: Xaa is 1-amino cyclopentane-1-carboxylic acid

<400> SEQUENCE: 51

His Glu Gln Trp Xaa Ser
1               5

<210> SEQ ID NO 52
<211> LENGTH: 7
<212> TYPE: PRT
<213> ORGANISM: Artificial
<220> FEATURE:
<223> OTHER INFORMATION: CD23 binding peptide

<400> SEQUENCE: 52

Ser Pro Trp Asn Glu His Phe
1               5

<210> SEQ ID NO 53
<211> LENGTH: 6
<212> TYPE: PRT
<213> ORGANISM: Artificial
<220> FEATURE:
<223> OTHER INFORMATION: CD23 binding peptide

<400> SEQUENCE: 53

His Glu Asn Ala Pro Ser
1               5

<210> SEQ ID NO 54
<211> LENGTH: 5
```

```
<212> TYPE: PRT
<213> ORGANISM: Artificial
<220> FEATURE:
<223> OTHER INFORMATION: CD23 binding peptide

<400> SEQUENCE: 54

His Glu Asn Trp Ser
1               5

<210> SEQ ID NO 55
<211> LENGTH: 5
<212> TYPE: PRT
<213> ORGANISM: Artificial
<220> FEATURE:
<223> OTHER INFORMATION: CD23 binding peptide
<220> FEATURE:
<221> NAME/KEY: MISC_FEATURE
<222> LOCATION: (1)..(1)
<223> OTHER INFORMATION: Xaa is glycine with allyl group -CH2-CH=CH2
<220> FEATURE:
<221> NAME/KEY: MISC_FEATURE
<222> LOCATION: (4)..(4)
<223> OTHER INFORMATION: Xaa is glycine with allyl group -CH2-CH=CH2

<400> SEQUENCE: 55

Xaa Asn Trp Xaa Ser
1               5

<210> SEQ ID NO 56
<211> LENGTH: 4
<212> TYPE: PRT
<213> ORGANISM: Artificial
<220> FEATURE:
<223> OTHER INFORMATION: CD23 binding peptide
<220> FEATURE:
<221> NAME/KEY: MISC_FEATURE
<222> LOCATION: (1)..(1)
<223> OTHER INFORMATION: Xaa is glycine with allyl group -CH2-CH=CH2
<220> FEATURE:
<221> NAME/KEY: MISC_FEATURE
<222> LOCATION: (4)..(4)
<223> OTHER INFORMATION: Xaa is glycine with allyl group -CH2-CH=CH2

<400> SEQUENCE: 56

Xaa Asn Trp Xaa
1

<210> SEQ ID NO 57
<211> LENGTH: 2
<212> TYPE: PRT
<213> ORGANISM: Artificial
<220> FEATURE:
<223> OTHER INFORMATION: CD23 binding peptide
<220> FEATURE:
<221> NAME/KEY: MISC_FEATURE
<222> LOCATION: (1)..(1)
<223> OTHER INFORMATION: Xaa is D-enantiomer of acetylated tryptophane
<220> FEATURE:
<221> NAME/KEY: MISC_FEATURE
<222> LOCATION: (2)..(2)
<223> OTHER INFORMATION: Xaa is D-enantiomer of asparagine

<400> SEQUENCE: 57

Xaa Xaa
1

<210> SEQ ID NO 58
<211> LENGTH: 2
<212> TYPE: PRT
<213> ORGANISM: Artificial
<220> FEATURE:
<223> OTHER INFORMATION: CD23 binding peptide
```

```
<220> FEATURE:
<221> NAME/KEY: MISC_FEATURE
<222> LOCATION: (1)..(1)
<223> OTHER INFORMATION: Xaa is acetylated asparagine

<400> SEQUENCE: 58

Xaa Trp
1

<210> SEQ ID NO 59
<211> LENGTH: 2
<212> TYPE: PRT
<213> ORGANISM: Artificial
<220> FEATURE:
<223> OTHER INFORMATION: CD23 binding peptide
<220> FEATURE:
<221> NAME/KEY: MISC_FEATURE
<222> LOCATION: (1)..(1)
<223> OTHER INFORMATION: Xaa is D-enantiomer of acetylated asparagine
<220> FEATURE:
<221> NAME/KEY: MISC_FEATURE
<222> LOCATION: (2)..(2)
<223> OTHER INFORMATION: Xaa is D-enantiomer of tryptophane

<400> SEQUENCE: 59

Xaa Xaa
1

<210> SEQ ID NO 60
<211> LENGTH: 3
<212> TYPE: PRT
<213> ORGANISM: Artificial
<220> FEATURE:
<223> OTHER INFORMATION: CD23 binding peptide
<220> FEATURE:
<221> NAME/KEY: MISC_FEATURE
<222> LOCATION: (1)..(1)
<223> OTHER INFORMATION: Xaa is acetylated asparagine
<220> FEATURE:
<221> NAME/KEY: MISC_FEATURE
<222> LOCATION: (3)..(3)
<223> OTHER INFORMATION: Xaa is beta-alanine

<400> SEQUENCE: 60

Xaa Trp Xaa
1

<210> SEQ ID NO 61
<211> LENGTH: 5
<212> TYPE: PRT
<213> ORGANISM: Artificial
<220> FEATURE:
<223> OTHER INFORMATION: CD23 binding peptide
<220> FEATURE:
<221> NAME/KEY: MISC_FEATURE
<222> LOCATION: (5)..(5)
<223> OTHER INFORMATION: Xaa is amidated proline

<400> SEQUENCE: 61

His Glu Asn Trp Xaa
1               5
```